(12) United States Patent
Schultes et al.

(10) Patent No.: US 6,689,355 B2
(45) Date of Patent: Feb. 10, 2004

(54) THERAPEUTIC METHOD AND COMPOSITION UTILIZING ANTIGEN-ANTIBODY COMPLEXATION AND PRESENTATION BY DENDRITIC CELLS

(75) Inventors: Birgit Corinna Schultes, Arlington, MA (US); Antoine Noujaim, Edmonton (CA); Dean L. Mann, Baltimore, MD (US)

(73) Assignee: AltaRex Corp., Edmonton (CA)

( * ) Notice: Subject to any disclaimer, the term of this patent is extended or adjusted under 35 U.S.C. 154(b) by 0 days.

(21) Appl. No.: 09/853,268

(22) Filed: May 11, 2001

(65) Prior Publication Data

US 2002/0164312 A1 Nov. 7, 2002

Related U.S. Application Data

(60) Provisional application No. 60/253,956, filed on Nov. 28, 2000, provisional application No. 60/253,671, filed on Nov. 28, 2000, and provisional application No. 60/203,635, filed on May 11, 2000.

(51) Int. Cl.$^7$ .......................... A01N 63/00; A01N 65/00; A61K 39/395; A61K 39/40; A61K 39/00; A61K 39/38

(52) U.S. Cl. ................ 424/93.1; 424/141.1; 424/155.1; 424/178.1; 424/184.1

(58) Field of Search ............................ 424/93.1, 178.1, 424/141.1, 155.1, 184.1

(56) References Cited

FOREIGN PATENT DOCUMENTS

| | | |
|---|---|---|
| DE | 19534630 A | 3/1997 |
| EP | 0553 244 B1 | 12/1998 |
| WO | WO 92/05793 | 4/1992 |
| WO | WO97/04802 A | 2/1997 |
| WO | WO99/65517 A | 12/1999 |
| WO | WO99/65523 A | 12/1999 |

OTHER PUBLICATIONS

Van Noort et al. International Review of Cytology, 1998.*
Steinman RM "The dendritic cell system and its role in immunogenicity" Annu Rev Immunol. 1991; 9:271–96.
Bjorck P "Development of dendritic cells and their use in tumor therapy" Clin Immunol. Aug. 1999; 92(2):119–27.
Avigan D "Dendritic cells: development, function and potential use for cancer immunotherapy" Blood Rev. Mar. 1999; 13(1): 51–64.
Timmerman JM, Levy R "Dendritic cell vaccines for cancer immunotherapy" Annu Rev Med. 1999; 50: 507–29.
Coughlan S et al., "Enhanced proliferation of CD4+ T cells induced by dendritic cells following antigen uptake in the presence of specific antibody" Vet Immunol Immunopathol. Jan. 1996; 49(4): 321–30.
Regnault A et al., "Fcgamma receptor–mediated induction of dendritic cell maturation and major histocompatibility complex class I–restricted antigen presentation after immune complex internalization" J Exp Med. Jan. 18, 1999; 189(2): 371–80.
M. Coccia et al., The Journal of Immunology, "High Titer, Prostate Specific Antigen–Specific Human IgG Production by hu–PBL–SCID Mice Immunized with Antigen–Mouse IgG2a Complex–Pulsed Autologous Dendritic Cells", 161:5772–5780, 1998.
B. Schultes et al., The FASEB Journal, "Induction of CA125–Specific B and T Cell Responses in MAb–B43.13 Injected Patients Depends on Complex Formation of the MAb with Circulating Antigen In Vivo", 14:A1003, 2000.
B. Schultes et al., Proceedings of the American Association for Cancer Research, "Antibody–Antigen Immune Complexes Allow for Efficient MHC Class I and II–Restricted Antigen Presentation and Maturation of Dendritic Cells: A Novel Strategy for Cancer Immunotherapy", 42:276, 2001.
International Search Report issued in connection with a counterpart Patent Cooperation Treaty Application No. PCT/IB01/01331.
International Search Report issued in connection with a counterpart Patent Cooperation Treaty Application No. PCT/IB01/01238.

* cited by examiner

*Primary Examiner*—Christina Chan
*Assistant Examiner*—Michail A Belyavskyi
(74) *Attorney, Agent, or Firm*—Ropes & Gray, LLP

(57) ABSTRACT

Disclosed are methods and compositions for use in immunotherapy. These methods and compositions are particularly useful for exploiting dendritic cells to present an antigen to a patient, particularly where the patient has a disease associated with the antigen. The invention provides methods for treating a patient having a disease associated with an antigen. The methods according to the invention comprise combining ex vivo an antigen and an antigen-presenting cell binding agent specific for the antigen, and administering the composition to a patient suffering from a disease associated with the antigen, wherein the patient receives a therapeutic benefit.

21 Claims, 22 Drawing Sheets

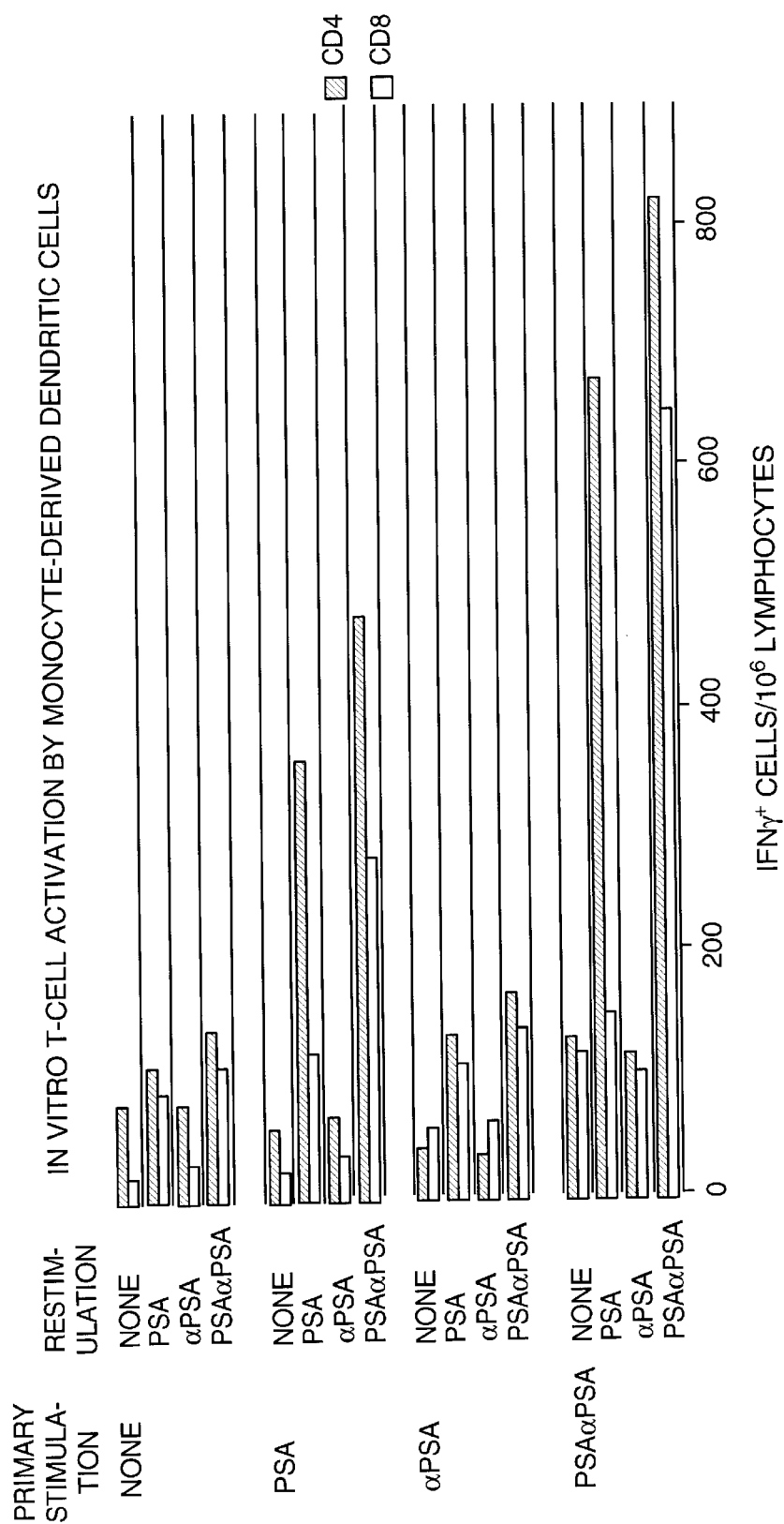

SEQUENCE LISTING

<160> NUMBER OF SEQ ID NOS: 4

<210> SEQ ID NO 1
<211> LENGTH: 10
<212> TYPE: PRT
<213> ORGANISM: Artificial Sequence
<220> FEATURE:
<223> OTHER INFORMATION: epitope of PSA

<400> SEQUENCE: 1

Glu Pro Glu Glu Phe Leu Thr Pro Lys Lys
1               5                   10

<210> SEQ ID NO 2
<211> LENGTH: 10
<212> TYPE: PRT
<213> ORGANISM: Artificial Sequence
<220> FEATURE:
<223> OTHER INFORMATION: HLA-A2 specific PSA peptide

<400> SEQUENCE: 2

Phe Leu Thr Pro Lys Lys Leu Gln Cys Val
1               5                   10

<210> SEQ ID NO 3
<211> LENGTH: 9
<212> TYPE: PRT
<213> ORGANISM: Artificial Sequence
<220> FEATURE:
<223> OTHER INFORMATION: HLA-A2 specific PSA peptide

<400> SEQUENCE: 3

Lys Leu Gln Cys Val Asp Leu His Val
1               5

<210> SEQ ID NO 4
<211> LENGTH: 8
<212> TYPE: PRT
<213> ORGANISM: Artificial Sequence
<220> FEATURE:
<223> OTHER INFORMATION: HIV-1 peptide

<400> SEQUENCE: 4

Ser Tyr Asn Thr Val Ala Val Leu
1               5

THERAPEUTIC METHOD AND COMPOSITION UTILIZING ANTIGEN-ANTIBODY COMPLEXATION AND PRESENTATION BY DENDRITIC CELLS

CROSS REFERENCE TO RELATED APPLICATION

This application claims the benefit of U.S. Provisional Application Serial No. 60/203,635 filed on May 11, 2000; U.S. Provisional Application Serial No. 60/253,956 filed Nov. 28, 2000; and U.S. Provisional Application Serial No. 60/253,671 filed Nov. 28, 2000 the entire contents of each of which are fully incorporated herein by reference.

GOVERNMENT SUPPORT

The research for the present invention was supported by a grant from the U.S. Army (DAMD 17-98-1-8644). The U.S. government has certain rights in this invention.

BACKGROUND OF THE INVENTION

1. Field of the Invention

The invention relates to immunotherapy. More particularly, the invention relates to the use of antigen presenting cells, in particular dendritic cells, in immunotherapy.

2. Summary of the Related Art

T lymphocytes (i.e., T cells), unlike B lymphocytes (i.e., B cells), typically recognize their target antigen only when the antigen is presented in the context of the major histocompatibility complex (MHC). Thus, to present antigen to T lymphocytes, which include T helper cells and cytotoxic T cells, the antigen must be presented in context of an MHC molecule on the surface of an antigen presenting cell.

In particular, one type of antigen presenting cell, dendritic cells, has recently become of interest in the area of cancer immunotherapy. Steinman, Annu. Rev. Immunol. 9: 271–296 (1991) teaches that dendritic cells are rare leukocytes that originate in the bone marrow and can be found distributed throughout the body. Bjork, Clinical Immunology 92: 119–127 (1999) teaches that dendritic cells receive increasing attention due to their potential inclusion as biological adjuvants in tumor vaccines. Dendritic cells express several receptors for the Fc portion of immunoglobulin IgG, which mediate the internalization of antigen-IgG complexes (ICs). In this capacity, dendritic cells are used to present tumor antigens to T cells. Avigan, Blood Reviews 13: 51–64 (1999) teaches that several approaches have been adopted to directly load tumor antigens onto dendritic cells, including the pulsing of tumor peptides onto mature dendritic cells. Timmerman et al., Annu. Rev. Med. 50: 507–529 (1999) teaches that isolated dendritic cells loaded with tumor antigen ex vivo and administered as a cellular vaccine have been found to induce protective and therapeutic anti-tumor immunity in experimental animals. European Patent No. EP0553244 describes an antigen/dual-specific binding agent complex for stimulating a response to the antigen, where the binding agent specifically binds both the antigen and a cell surface receptor on an antigen-presenting cell, but where binding of the binding agent to the cell surface receptor does not block the natural ligand for the receptor.

The mechanism of action for dendritic cell antigen presentation has also been explored. Coughlan et al., Veterinary Immunology and Immunopathology 49: 321–330 (1996) discloses that antigen uptake by dendritic cells via Fcγ receptors results in functional augmentation of antigen presentation and T cell proliferation in an in vitro sheep system. Regnault et al., J. Exp. Med. 189: 371–380 (1999) teaches that Fcγ receptors induce dendritic cell maturation and promote efficient MHC class I-restricted presentation of peptides from exogenous, immunoglobulin (Ig) complexed antigens in the mouse system.

Thus, there remains a need to discover methods for utilizing dendritic cells to treat human diseases. The promise of dendritic cell-based approaches to treat diseases, such as cancer, underscores the need to actually develop such approaches as effective therapeutic treatments.

BRIEF SUMMARY OF THE INVENTION

The invention provides a therapeutically effective dendritic cell-based approach to the treatment of diseases associated with an antigen. The methods according to the invention comprise combining ex vivo an antigen associated with a disease and a dendritic cell binding agent specific for the antigen, with or without a dendritic cell, to provide a composition, and administering the composition to a patient having a disease associated with the antigen, wherein the composition-administered patient receives a therapeutic benefit.

Accordingly, in a first aspect, the invention provides a method for treating a patient suffering from a disease associated with an antigen, comprising administering to the patient suffering from the disease a composition comprising an antigen associated with the disease and a dendritic cell binding agent specific for the antigen, wherein the antigen is complexed to the dendritic cell binding agent and wherein the patient administered the composition receives a therapeutic benefit. Preferably, the patient is human.

In a second aspect, the invention provides a method for treating a patient suffering from a disease associated with an antigen, comprising administering to the patient a composition comprising an antigen associated with the disease, a dendritic cell binding agent specific for the antigen, and a dendritic cell autologous to the patient, wherein the patient administered the composition receives a therapeutic benefit. Preferably, the patient is a human.

In a third aspect, the invention provides a method for treating a patient suffering from a disease associated with an antigen, comprising administering to the patient suffering from the disease a composition comprising a host anti-xenotypic antibody and a xenotypic antibody specific for the antigen associated with the disease, wherein the patient administered the composition receives a therapeutic benefit.

In a fourth aspect, the invention provides a therapeutic composition comprising a purified dendritic cell binding agent that is specific for an antigen associated with a disease and the antigen associated with the disease. In preferred embodiments, binding of the dendritic cell binding agent to a receptor on a dendritic cell blocks binding of a natural ligand to the receptor. In certain embodiments of the fourth aspect of the invention, administration of the composition to a patient suffering from the disease provides the patient a therapeutic benefit. Preferably, the patient is a human. Preferably, the dendritic cell binding agent is an antibody.

In a fifth aspect, the invention provides a therapeutic composition comprising a purified dendritic cell binding agent that is specific for an antigen associated with a disease, a dendritic cell, and the antigen associated with the disease. In preferred embodiments, binding of the dendritic cell binding agent to a receptor on the dendritic cell blocks binding of a natural ligand to the receptor. In certain embodiments, administration of the composition to a patient suffering from the disease provides the patient a therapeutic benefit, wherein the dendritic cell is autologous to the patient. Preferably, the patient is human In a sixth aspect, the invention provides a therapeutic composition comprising a purified xenotypic antibody that is specific for an antigen associated with a disease and a host anti-xenotypic antibody. In certain embodiments, administration of the composition to a patient suffering from the disease provides the patient a therapeutic benefit, wherein the dendritic cell is autologous to the patient. Preferably, the patient is human

BRIEF DESCRIPTION OF THE DRAWINGS

FIG. 1A is a bar graph showing the percentage of positive events of monocytes or immature dendritic cells following incubation with 1000 U/ml FITC-labeled CA125 antigen and the indicated amount of Alt-2 antibody. FIG. 1B is a bar graph showing the mean channel intensity of monocytes or immature dendritic cells following incubation with 1000 U/ml FITC-labeled CA125 antigen and the indicated amount of Alt-2 antibody.

FIG. 4A shows the binding of FITC-labeled anti-CA125 antibody, Alt-2, or FITC-labeled anti-PSA antibody, Alt-G, to dendritic cells in the presence or absence antigen or in the presence or absence of HAMA. FIG. 4B shows the binding of the FITC labeled Alt-2 in the presence of 8000 U/ml CA125 when the concentration of Alt-2 is 0, 0.313, 0.625, 1.25, and 2.5 µg/ml. FIG. 4C show the binding of 1 µg/ml FITC labeled Alt-2 in the presence of 8000 U/ml CA125 with or without human anti-mouse antibody (HAMA) at 0, 0.33, 1, and 2 µg/ml.

FIG. 6 is a bar graph showing the in vitro T cell activation (both CD4+ and CD8+ T cells by dendritic cells "armed" by the indicated primary stimulation and restimulation as determined by the number of IFNγ producing cells per $10^6$ cells.

FIG. 10A is a bar graph comparing the levels of CA125/αCA125 complex compared to the level of free circulating CA125. FIG. 10B is a line graph showing the rate of complexation of anti-CA125 antibody, Alt-2, to circulating CA125 following injection of Alt-2 (left side of the graph), and the amount of free Alt-2 antibody cleared following injection time, as measured in percentage of the injected dose (% ID). With time, the percentage of free circulating CA125 decreases as the amount of complexed CA125 increases.

FIG. 11A shows the induction of humoral anti-CA125 response (y-axis) as compared to the level of circulating CA125 antigen present at the time of injection of the anti-CA125 antibody, Alt-2 (x-axis). FIG. 11B shows the induction of a cellular anti-CA125 response (y-axis) as compared to the level of circulating CA125 antigen (x-axis), comparing pre-injection of Alt-2 (open triangles) to post-injection of Alt-2 (closed triangles). FIG. 11C is a scatter graph showing the stimulation index of T cells (CA125-specific T cell proliferation) in patient before (pre) or after (post) Alt-2 injection, where patients having greater than 105 U/ml CA125 had the greatest T cell response.

FIG. 13A is a survival curve showing an increased survival in patients who developed a 3× increase in anti-CA125 antibody response following injection of Alt-2 (dotted line) as compared to those with developed a less than 3× increase in anti-CA125 antibody response following injection of Alt-2 (solid line). FIG. 13B is a survival curve showing an increased survival in patients who developed a CA125-specific T cell response following injection of Alt-2 (dotted line) as compared to those who did not develop a CA125-specific T cell response following injection (solid line).

FIG. 14A is a bar graph showing the level of T cell proliferation as measured by the Stimulation Index (SI) using macrophages as antigen-presenting cells following stimulation by the CA125, Alt-2, B27.1, mIgG1, CA125 plus Alt-2, CA125 plus B27.1, and CA125 plus mIgG1 at 0.1 µg/ml, 1 µg/ml and 10 µg/ml. FIG. 14B is a bar graph showing the level of T cell stimulation as measured by the Stimulation Index (SI) using B cells as antigen-presenting cells following stimulation by the CA125, Alt-2, B27.1, mIgG1, CA125 plus Alt-2, CA125 plus B27.1, and CA125 plus mIgG1 at 0.1 µg/ml, 1 µg/ml, and 10 µg/ml.

DETAILED DESCRIPTION OF THE PREFERRED EMBODIMENTS

Figure 1B:
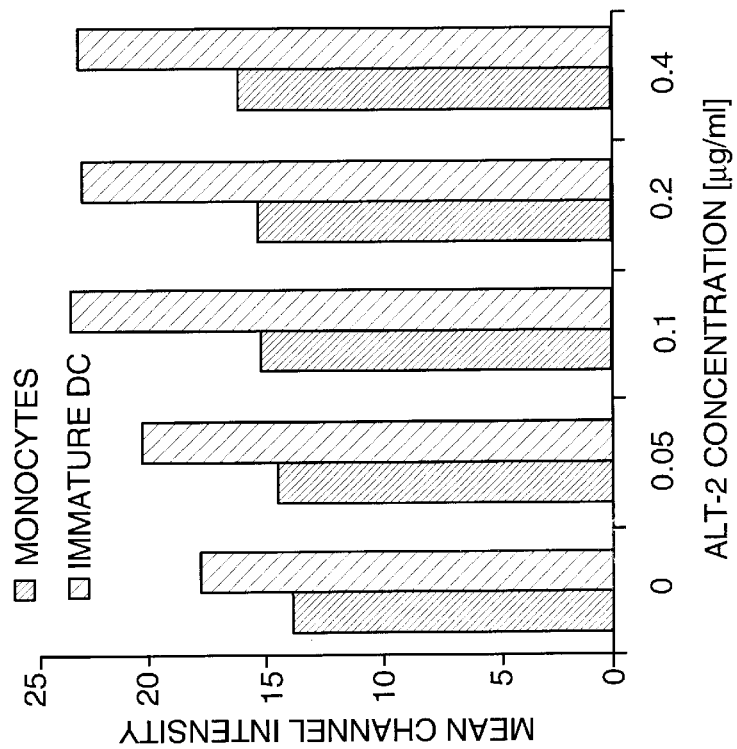
FIGS. 1A and 1B show the results of antigen binding studies with monocytes and immature dendritic cells.

The invention relates to immunotherapy. More particularly, the invention relates to the use of antigen-presenting cells, in particular dendritic cells, in immunotherapy. The invention provides a therapeutically effective dendritic-based approach to the treatment of diseases associated with an antigen. The patents and publications cited herein reflect the level of skill in this field and are hereby incorporated by reference in their entirety to the same extent as if each was specifically and individually indicated to be incorporated by reference. In the case of any conflict between a cited reference and this specification, this specification shall prevail.

The invention provides methods for treating a patient having a disease associated with an antigen. The methods according to the invention comprise combining ex vivo the antigen associated with the disease with a dendritic cell binding agent specific for the antigen to provide a composition, and administering the composition to a patient suffering from the disease associated with the antigen, wherein the patient receives a therapeutic benefit.

Accordingly, in a first aspect, the invention provides a method for treating a patient suffering from a disease associated with an antigen, comprising administering to the patient suffering from the disease a composition of an antigen associated with the disease and a dendritic cell binding agent specific for the antigen, wherein the antigen is complexed to (i.e., specifically bound by) the dendritic cell binding agent, and wherein the patient administered the composition receives a therapeutic benefit.

In certain embodiments, an antigen/dendritic cell binding agent complex may be formed, for example, by combining ex vivo the antigen and the dendritic cell binding agent. By "combining ex vivo" means bringing into physical proximity outside of the body.

In certain preferred embodiments, the patient is a human. In other embodiments, the patient is preferably a non-human mammal, particularly a laboratory animal. Preferred non-human patients of the invention include, without limitation, mice, rats, rabbits, non-human primates (e.g., chimpanzees, baboons, rhesus monkeys), dogs, cats, pigs, and armadillos.

The methods according to the invention are useful for therapeutically treating patients having a disease associated with an antigen. As used herein, the term "disease associated with an antigen" means a condition in which signs or symptoms of illness in a majority of patients are present when the antigen is present in the patient's body at a certain concentration, but in which signs or symptoms of illness are absent or reduced when the antigen is absent from the patient's body or present in the patient's body at a lower concentration. "Signs or symptoms of illness" are clinically recognized manifestations or indications of disease.

It will be appreciated that a "patient suffering from a disease associated with an antigen" of the invention may not yet be symptomatic for the disease. Accordingly, a patient with circulating BRCA-1 is a patient according to the invention even though that patient may not yet be symptomatic for breast cancer or other adenocarcinoma.

Some non-limiting examples of such antigens associated with a disease include the prostate specific antigen (associated with prostate cancer), BRCA-1 and BRCA-2 antigens (associated with many adenocarinomas, including breast cancer, lung cancer, and pancreatic cancer), CA125 (associated with ovarian cancer), aberrant myelin basic protein (associated with Alzheimer's disease), gp120 (associated with HIV infection and AIDS), MUC-1 (associated with breast cancer), EBNA-1 (associated with Epstein Barr Virus infection), CA19.9 (associated with colorectal, stomach, and pancreatic cancers), and TAG-72 (associated with ovarian, stromal, and pancreatic cancers), p53 (associated with various cancers).

Thus, in certain preferred embodiments, the antigen is a tumor-associated antigen. A "tumor associated antigen" is an antigen in the patient's body that is made by tumor cells, and which may be presented on the tumor surface, or circulating, or both. Preferred tumor-associated antigens include, without limitation, CA125, PSA, MUC-1, CA19.9, and TAG-72. Generally from about 0.1 to about 50 μg antigen are used.

In certain preferred embodiments, the antigen is from a pathogen. A "pathogen" is an etiolytic agent capable of causing disease. Preferred pathogens include, without limitation, viruses (e.g. hepatitis B, hepatitis C, herpes, and HIV-1), viroids, bacteria, fungi, prions, and parasites.

"Specifically bound to the antigen" or "specific for the antigen" means that the dendritic cell binding agent binds to the antigen with greater affinity than it binds unrelated proteins. Preferably such affinity is at least 10-fold greater, more preferably at least 100-fold greater, and most preferably at least 1000-fold greater than the affinity of the binding agent for unrelated proteins. Preferably, an antigen presenting cell binding agent that is specific for an antigen forms an association with that antigen with an affinity of at least $10^6$ $M^{-1}$, more preferably, at least $10^7$ $M^{-1}$, even more preferably, at least $10^8$ $M^{-1}$, even more preferably, at least $10^9$ $M^{-1}$, and most preferably, at least $10^{10}$ $M^{-1}$ either in water, under physiological conditions, or under conditions which approximate physiological conditions with respect to ionic strength, e.g., 140 mM NaCl, 5 mM $MgCl_2$.

The injected dendritic cell binding agent complexed to a circulating antigen is targeted in vivo to dendritic cells (which are preferably immature dendritic cell) through Fc receptors present on the surface of these dendritic cells. By targeting antigen to preferably immature dendritic cells and presentation of these antigens on both MHC class I and class II molecules, the immune complex of the binding agent/antigen efficiently sensitize dendritic cells to induce activation of both CD4(+) helper and CD8(+) cytotoxic T cells in vivo.

A "dendritic cell binding agent" of the invention binds to the ligand-binding site of a receptor on the surface of a dendritic cell, at any stage of development of the dendritic cell. Preferably, once the dendritic cell binding agent is bound to the ligand-binding site of the dendritic cell receptor, the natural ligand cannot bind to the receptor at the same time that the dendritic cell binding agent binds to the receptor. Preferably, the dendritic cell binding agent binds to the receptor on the surface of a dendritic cell when the binding agent is specifically bound to an antigen. Preferably, such binding causes internalization of the binding agent/antigen complex. Even more preferably, binding and/or internalization of the binding agent/antigen complex by an immature or precursor dendritic cell causes maturation and/or activation of the dendritic cell.

Preferably, the dendritic cell binding agent of the invention binds to an activating Fcγ receptor, such as CD64 (FcγRI) or CD32 (FcγRIIA) that is not abundant on neutrophils.

As used herein, by "ligand-binding site of a receptor" is meant the site on the receptor to which the natural ligand of the receptor binds. For example, if the receptor is a Fcγ type II receptor, the natural ligand for the receptor is an IgG antibody. A dendritic cell binding agent of the invention, when bound to a receptor, blocks the ligand-binding site of the receptor such that the natural ligand for that receptor cannot bind the receptor. In one non-limiting example, if the receptor is a Fcγ type II receptor and the dendritic cell binding agent of the invention is an IgG antibody, then binding of the dendritic cell binding agent of the invention to the receptor prevents other IgG antibodies from binding to the receptor.

Accordingly, dendritic cell binding agents of the invention are readily identified by art-known methods. In one non-limiting example, where the dendritic cell binding agent is an IgG antibody, a precursor, immature, or mature dendritic cell is purified as described below. Next, the cell is incubated with the FITC-labeled IgG antibody (with or without the antigen to which the antibody specifically binds). Next, the phycoerythrin (PE)-labeled natural ligand (i.e., another IgG antibody) is added to the cell. The cell can then be subjected to analysis by flow cytometry to determine if the FITC-labeled IgG antibody of the invention is able to block binding of the PE-labeled antibody to the receptor on the dendritic cell.

In certain preferred embodiments, the dendritic cell binding agent is not a bispecific antibody which has two antigen binding sites, one that is specific for the antigen of the invention and the other that is specific for the receptor, e.g., at its ligand-binding site, on the surface of a dendritic cell.

"Administering the composition to a patient" means providing the composition to the patient in a manner that results in the composition being inside the patient's body. Such an administration can be by any route including, without limitation, sub-cutaneoous, intradermal, intravenous, intra-arterial, intraperitoneal, and intramuscular. "Receives a therapeutic benefit" means that the patient experiences alleviation or reduction of signs or symptoms of illness, and specifically includes, without limitation, prolongation of survival. In certain preferred embodiments of the methods according to the invention, a CD8+ IFN-γ producing T cell is activated to induce a cytotoxic T lymphocyte (CTL) immune response in the patient administered the composition. In certain embodiments of the methods according to the invention, a CD4+ IFN-γ producing T cell is activated to induce a helper T cell immune response in the patient administered with the composition. These activated CD4+ IFN-γ producing T cells (i.e., helper T cells) provide necessary immunological help (e.g., by release of cytokines) to induce and maintain not only CTL, but also a humoral immune response mediated by B cells. Thus, in certain embodiments of the methods according to the invention, a humoral response to the antigen is activated in the patient administered with the composition.

Activation of a CD8+ and/or CD4+ IFN-γ producing T cells means causing T cells that have the ability to produce IFN-γ to actually produce IFN-γ, or to increase their production of IFN-γ. "Induction of CTL" means causing potentially cytotoxic T lymphocytes to exhibit antigen-specific cytotoxicity, or to increase such antigen-specific cytotoxocity. "Antigen-specific cytotoxicity" means cytotoxicity against a cell that is presenting the antigen that is greater than cytotoxicity against a cell that is not presenting the antigen. "Cytotoxicity" refers to the ability of the cytotoxic T lymphocyte to kill the target cell. Preferably, such antigen-specific cytotoxicity is at least 3-fold, more preferably 10-fold greater, more preferably more than 100-fold greater than cytotoxicity against a cell that is not presenting the antigen.

In certain preferred embodiments, the dendritic cell binding agent of the invention binds to the antigen and an Fcγ type II or type I receptor on the dendritic cells. Preferably, binding of the binding agent to the Fcγ type II or type I receptor blocks the binding of the natural ligand to, respectively, the Fcγ type II or type I receptor. Accordingly, in certain embodiments, the dendritic cell binding agent binds to the antigen and to an Fcγ Type I (CDG4) receptor on a dendritic cell in the patient administered with the composition. In certain embodiments, the dendritic cell binding agent binds to the antigen and to an Fcγ Type II (CD32) receptor, such as a Fcγ Type IIA (CD32A) receptor or a Fcγ Type IIB (CD32B) receptor on a dendritic cell in the patient administered with the composition. In certain embodiments, the dendritic cell binding agent binds to the antigen and to an Fcγ Type III (CD16) receptor on a dendritic cell in the patient administered with the composition.

In certain preferred embodiments, the dendritic cell binding agent of the invention is an antibody. Preferably the antibody is provided at a concentration of from about 1–10 µg/ml. An "antibody" includes a molecule comprising an active portion of an antibody. "An active portion of an antibody" is a molecule that includes an antigen binding site that is specific for an antigen and a receptor binding site that binds an Fc receptor on its ligand-binding site (e.g., the Fc portion of the antibody included the heavy chain constant region). Accordingly, an antibody of the invention may be, e.g., chimeric, single chain, mutant, or antibody fragment so long as the antibody is able to specifically bind an antigen and so long as the antibody includes a portion that binds an Fc receptor on its ligand-binding site.

Accordingly, an antibody of the may be encoded by an immunoglobulin gene having specific point mutation in the part of the gene encoding the receptor binding site. In one non-limiting example, the gene encoding the anti-PSA antibody, Alt-6, can be subjected to point mutation in the portion of the gene encoding the receptor binding site. The resulting antibody mutants can be screened on cells (e.g., COS or HeLa cells) transfected with a gene encoding the Fcγ Type I (CDG4) receptor, the Fcγ Type II (CD32) receptor, or the Fcγ Type III (CD16) receptor. A preferred mutant Alt-6 antibody of the invention is one which binds better (i.e., by greater numbers or with higher affinity) to a cell expressing the Fcγ Type I (CDG4) receptor, Fcγ Type II (CD32) receptor and/or the Fcγ Type III (CD16) receptor as compared to a cell not expressing one of these receptors.

In certain embodiments, the dendritic cell binding agent of the composition includes a portion that elicits a human anti-xenotypic antibody (HAXA) response.

In certain embodiments, the dendritic cell binding agent is a xenotypic antibody. A "xenotypic antibody" is an antibody from a species other than the patient's species. For example, if the patient is a human, a dendritic binding agent of the invention that is a murine antibody is a xenotypic antibody. Similarly, if the patient is a mouse, a dendritic binding agent of the invention that is a rat antibody is a xenotypic antibody. Preferred xenotypic antibodies include monoclonal antibodies, including without limitation murine monoclonal antibodies. Particularly preferred murine monoclonal antibodies include Alt-1 (murine IgG1, specifically binds to MUC-1; ATCC No. PTA-975;American Type Culture Collection, Manassas, Va.), Alt-2 (murine IgG1, specifically binds to CA125; ATCC No. PTA-1883, deposited on May 18, 2000; American Type Culture Collection, 10801 University Blvd., Manassas, Va. 20110), Alt-3 (murine IgG3, specifically binds to CA19.9; ATCC No. PTA-2691), Alt-4 (murine IgM, specifically binds to CA19.9; ATCC No. PTA-2692), Alt-5 (murine IgG1, specifically binds to CA19.9; ATCC No. PTA-2690); and Alt-6 (murine IgG1, specifically binds to prostate specific antigen (PSA); ATCC No. HB-12526, deposited on Apr. 29, 1998; American Type Culture Collection, Manassas, Va.)

In certain embodiments, the xenotypic antibody elicits a host anti-xenotypic antibody (HAXA) response in the patient.

In certain preferred embodiments, the composition administered to the patient further includes host anti-xenotypic antibodies (HAXA). "Host anti-xenotypic antibodies (HAXA)" are antibodies of the host animal species that bind to the xenotypic antibody contained in the composition of the invention. For example, if the patient is a human and the xenotypic antibodies are rabbit antibodies, the HAXA is human anti-rabbit antibodies. Preferably the HAXA is provided in the composition at a concentration of from about 1–10 μg/ml. Preferred HAXA include, without limitation, human anti-mouse antibody (HAMA).

In certain embodiments, if the composition administered to the patient does not include HAXA, HAXA is preferably already present in the patient's blood. Such a patient may already have HAXA if, for example, the patient has been previously treated with a non-specific antibody of the same species as the dendritic cell binding agent of the invention. For example, prior to the administration of the composition of the invention comprising the dendritic cell binding agent and the antigen, a human patient may be administered with a polyclonal murine antibody with no defined specificity (or with a murine monoclonal antibody that specifically binds to, for example, an egg shell protein not expressed in humans). Once HAMA is detectable in the patient's blood, the composition is administered to the patient.

In further embodiments, the composition of the first aspect further comprises a dendritic cell. Preferably, the dendritic cell is autologous to the patient.

As used herein, by "dendritic cell" is meant a bone marrow-derived cell that can internalize antigen and process the antigen such that it (or a peptide derived from the antigen) is presented in the context of both the MHC class I complex and the MHC class II complex. Accordingly, a dendritic cell of the invention is able to activate both CD8+ T cells (which are primarily cytotoxic T lymphocytes) and CD4+ T cells (which are primarily helper T cells). It should be understood that any cell capable of presenting a peptide derived from an internalized antigen on both class I and class II MHC is a dendritic cell of the invention. Preferably, a dendritic cell of the invention has the phenotype and characteristics of the dendritic cells described in Steinman, Annu. Rev. Immunol. 9: 271–296 (1991).

In certain preferred embodiments, the dendritic cell, when added to the composition, is an immature dendritic cell. As used herein, by "immature dendritic cells" means a population of dendritic cells preferably having one or more of the following cell surface antigens at the indicated level of expression: CD11c present on greater than about 90% of the dendritic cells in the population, HLA-DR present on fewer than about 90% of the dendritic cells in the population but on greater than about 70% of the dendritic cells in the population, HLA-ABC present on from about 80% to about 90% of the dendritic cells in the population, CD 14 present on fewer than about 20% of the dendritic cells in the population, CD16 present on greater than about 10% to about 40% of the dendritic cells in the population, CD80 present on about 50% to about 70% of the dendritic cells in the population, CD86 present on greater than about 40% to about 70% of the dendritic cells in the population, CD83 present on greater than about 10% to about 20% of the dendritic cells in the population, CD64 present on greater than about 40% to about 60% of the dendritic cells in the population, and CD32 antigen present on from about 70% to about 95% of the dendritic cells in the population, and about less than 10% of the dendritic cells in the population are CD3/CD19 positive (i.e., about less than 10% have CD3/CD19 expression).

In certain preferred embodiment, the dendritic cell, when added to the composition, is a precursor dendritic cell. As used herein, by "precursor dendritic cells" means a population of cells, each of which is capable of becoming a dendritic cell, where greater than 80% of the population have CD64 and CD32 antigen present and about 70% of the population is positive for CD14.

In the embodiments of the invention where the dendritic cell, when added to the composition, is either an immature dendritic cell or is a precursor dendritic cell, the composition is preferably incubated ex vivo under conditions (e.g., in cell culture) that allow for maturation of the immature dendritic cell or precursor dendritic cell prior to administering the composition to the patient. Such conditions that allow the formation of mature dendritic cells from immature or precursor dendritic cells are described below in the examples.

In the embodiments of the invention where the dendritic cell is included in the composition, and where the patient is human, the dendritic cell preferably expresses the cell surface molecules described below in Table I at its different maturation stages. Note that expression of the Fc receptors, particularly the CD64 (FcγRI) typically decreases as the DC mature.

TABLE I

Human Dendritic Cell Surface Markers

| | Day 0 Monocytes | Day 4 immature DC | Day 7 mature DC |
|---|---|---|---|
| Marker (all cells) | | | |
| HLA-DR | 70–85% | 80–85% | 95–99% |
| HLA-ABC | 70–85% | 85–90% | 95–99% |
| CD3 | 1–5% | ND | ND |
| CD4 | 2–3% | ND | ND |
| CD8 | 2–3% | ND | ND |
| CD16 | 3–15% | 15–40% | 0.5–5% |
| CD19 | 5–10% | ND | ND |
| CD14 | 75–80% | 0.4–0.5% | 0.1–0.2% |
| CD11c | 75–80% | 95–99% | 99–100% |
| Marker (gated on DC) | | | |
| CD86 | 85–90% | 40–70% | 95–99% |
| CD80 | 30–50% | 55–80% | 85–90% |
| CD40 | 40–50% | 55–60% | 55–60% |
| CD83 | 10–15% | 10–15% | 55–60% |
| CD32 | 89–98% | 70–95% | 40–45% |
| CD64 | 92–99% | 28–60% | 4–10% |

One non-limiting method to obtain dendritic cells according to the invention is described below in Example I.

Accordingly, in one non-limiting method, 10 μg of CA125 and 5 μg of the murine monoclonal antibody that specifically binds to CA125, Alt-2, are combined together ex vivo. In a variation of the method, human anti-murine antibodies are added to the mixture. Then, the mixture is added to immature dendritic cells prepared as described below from the patient suffering from the disease. The addition of the antigen (in this case CA125 plus αCA125 antibody, Alt-2) promotes maturation of the immature dendritic cells. (Note that as used throughout, the symbol "α" means "anti-". Thus, "αCA125" means "anti-CA125"). Next, the matured dendritic cells "loaded" or "armed" with CA125 and Alt-2 (and, in some cases, HAMA) are removed from culture and administered to the patient.

Note that the dendritic cell used in the invention is preferably autologous to the patient to whom the composition of the invention is administered. By "autologous" is meant having identically matched MHC loci (both class I and class II). Thus, an identical sibling can provide autologous dendritic cells for a patient. Similarly, a close relative can provide autologous dendritic cells for a patient, so long as the patient and the close relative have identically matched MHC loci. Of course, two individuals of an inbred strain of laboratory animal (e.g., inbred Balb/c mice) are autologous to one another.

In certain preferred embodiments, if the patient to whom the composition of the invention is administered already had an immune response to the antigen, following administration, the immune response is shifted predominantly from a helper to a cytotoxic T cell response, thus providing the patient, following administration, a therapeutic benefit Thus, in one non-limiting example, a patient of the invention with prostate cancer may already have either antibodies that are specific for prostate specific antigen (PSA) and/or helper T cells that are specific for PSA. However, following administration of the composition of the invention, the PSA of the composition is internalized and presented on antigen presenting cells in such a way (e.g., in context of MHC class I) that cytotoxic T cells that are specific for PSA are stimulated, thereby providing the patient a therapeutic benefit as compared to the patient's condition prior to administration of the composition.

In a second aspect, the invention provides a method for treating a patient suffering from a disease associated with an antigen, comprising administering to the patient a composition comprising an antigen associated with the disease, a dendritic cell binding agent specific for the antigen, and a dendritic cell autologous to the patient, wherein the patient administered the composition receives a therapeutic benefit. Preferably, the patient is a human In some embodiments, the dendritic cell, when combined with the antigen and the dendritic cell binding agent, is either a precursor dendritic cell or an immature dendritic cell. In these embodiments, the composition is incubated ex vivo under conditions that allow for maturation of the immature dendritic cell prior to administering the composition to the patient.

In some embodiments, the antigen and dendritic cell binding agent may be combined simultaneously with the dendritic cell to make the composition. In some embodiments, the dendritic cell binding agent and the antigen are combined with one another before they are combined with the dendritic cell to make the final composition. In these embodiments, the composition including the dendritic cell is then administered to the patient suffering from the disease.

In certain embodiments, where the dendritic cell binding agent is a xenotypic antibody and the composition further comprises human anti-xenotypic antibodies.

In a third aspect, the invention provides a method for treating a patient suffering from a disease associated with an antigen, comprising administering to the patient suffering from the disease a composition comprising a host anti-xenotypic antibody and a xenotypic antibody specific for the antigen associated with the disease, wherein the patient administered the composition receives a therapeutic benefit.

In a fourth aspect, the invention provides a therapeutic composition comprising a purified dendritic cell binding agent that is specific for an antigen associated with a disease and the antigen associated with the disease. Preferably, binding of the dendritic cell binding agent to a receptor on a dendritic cell blocks binding of a natural ligand to the receptor.

In a fifth aspect, the invention provides a therapeutic composition comprising a purified dendritic cell binding agent that is specific for an antigen associated with a disease, a dendritic cell, and the antigen associated with the disease. Preferably, binding of the dendritic cell binding agent to a receptor on the dendritic cell blocks binding of a natural ligand to the receptor. Preferably, the dendritic cell of the composition is autologous to a patient to whom the composition is administered.

In a sixth aspect, the invention provides a therapeutic composition comprising a purified xenotypic antibody that is specific for an antigen associated with a disease and a host anti-xenotypic antibody.

As used herein, by "purified" is meant that the indicated agent (e.g., a purified dendritic cell binding agent or xenotypic antibody) has been separated from components which naturally accompany it. For example, in the case of a protein (e.g., a dendritic cell binding agent), the purified protein is separated from components, such as other proteins or fragments of cell membrane, that accompany it in the cell. Of course, those of ordinary skill in molecular biology will understand that water, buffers, and other small molecules may additionally be present in a purified protein preparation. A purified protein (e.g., a purified dendritic cell binding agent) of the invention is at least 95% by weight, more preferably at least 98% by weight, even more preferably at least 99% by weight, and most preferably 100% by weight free of components which naturally accompany the nucleic acid molecule or polypeptide.

According to the invention, a purified dendritic cell binding agent of the invention may be generated, for example, by recombinant expression of a nucleic acid molecule encoding the dendritic cell binding agent in a cell in which the dendritic cell binding agent does not naturally occur. Of course, other methods for obtaining a purified dendritic cell binding agent of the invention include, without limitation, artificial synthesis of the dendritic cell binding agent on a peptide synthesizer and isolation of the dendritic cell binding agent from a cell in which it naturally occurs using, e.g., an antibody that specifically binds to the dendritic cell binding agent. In the case where the dendritic cell binding agent is a monoclonal antibody, a purified dendritic cell binding agent can be obtained from the culture supernatant of the hybridoma which secretes the dendritic cell binding agent, or from ascites fluid from an animal injected with the hybridoma.

Preferably, the therapeutic compositions of the fourth, fifth, and sixth aspects of the invention further comprise a pharmaceutically acceptable carrier. By "pharmaceutically acceptable carrier" is meant a carrier that is physiologically acceptable to the administered patient and that retains the therapeutic properties of the dendritic cell binding agent and antigen (and/or dendritic cell) with which is it administered. One exemplary pharmaceutically acceptable carrier is physiological saline. Other pharmaceutically-acceptable carriers and their formulations are well-known and generally described in, for example, *Remington's Pharmaceutical Sciences* (18th Edition, ed. A. Gennaro, Mack Publishing Co., Easton, Pa., 1990).

Preferably, administration of the therapeutic compositions of the fourth, fifth, and sixth aspects of the invention to a patient suffering from the disease provides the patient a therapeutic benefit. Preferably, the patient is a human.

The following examples are intended to further illustrate certain particularly preferred embodiments of the invention and are not intended to limit the scope of the invention.

Example I

Isolation of Dendritic Cells

To isolate dendritic cells, peripheral blood mononuclear cells (PBMC) were isolated from the apheresis products from normal volunteers by ficoll-hypaque (Histopaque 1.077, commercially available from Sigma, St. Louis, Mo.) gradient centrifugation, and viably frozen using an automated cell freezer (commercially available from Gordinier Electronics, Roseville, Mich.) in RPMI (commercially available from Life Technologies, Frederick, Md.) containing 40% human antibody serum (commercially available from Gemini Bio-Products, Woodland, Calif.) and 10% DMSO (Sigma). The cells were stored in the vapor phase of liquid nitrogen until used. DNA was prepared from a portion of the cells and used for molecular HLA typing.

Next, dendritic cells (DC) were isolated by negative selection. To do this, DC precursors were prepared from freshly-thawed PBMC by negative selection using immunomagnetic bead depletion. Specifically, PBMC were placed into a tube and incubated on ice for 30 min. with mouse anti-human CD3, CD16, and CD19 antigens (commercially available from Caltag, Burlingame, Calif.). Excess antibody was removed by washing the cells with phosphate buffered saline containing 1% of bovine serum albumin (PBS/0.1% BSA), and the washed cells were next incubated with Pan Mouse IgG immunomagnetic beads (commercially available from Dynal, Lake Success, N.Y.) for 30 min. on ice. The tube containing the cells plus specific mouse anti-human antigens and the Pan Mouse IgG immunomagnetic beads was placed against a magnet to remove the cell:bead complexes. The cells that bound to the magnet were either T cells, B cells, or Natural Killer (NK) cells. Accordingly, the supernatant contained the lineage-depleted DC precursors (i.e., the monocytes remaining in the fluid in the tube not expressing CD3, CD16, or CD19 antigens and so not bound by the magnet). These negatively selected cells were approximately 70% pure monocytes as characterized by Flow cytometry using a broad CD marker panel (see Table I above) were collected.

Next, the negatively selected cells were washed, resuspended in cRPMI (RPMI supplemented with 1% glutamine and 10% heat-inactivated human serum (from a person with blood type AB)) containing GM-CSF (1000 U/ml) and IL-4 (1000 U/ml) (both commercially available from R & D Systems, Minneapolis, Minn.) and cultured at 37° C. in 5% $CO_2$ at $0.5 \times 10^6$ cells/well in 24 well plates for four days. These cells were immature dendritic cells by day four, and analyzed for surface expression of numerous cell surface antigens by flow cytometry see Table I above).

On the fourth day of culture, the cells were pulsed with antigen (e.g., Prostate Specific Antigen (PSA)) and incubated for an additional three days. (Note that the antigen which the DC cells were pulsed with was dependent upon what the DC cells would be eventually used for. For example, if the DC cells were to be used to generate a T cell response to PSA, the DC cells would be pulsed with PSA antigen.) Several agents which are known to cause DC precursors to mature into mature DC cells were added to the cultures eight hours after addition of the antigen. These agents included TNFα (10 μg/ml) and/or IFNα (50 μg/ml). The matured DC were harvested on the seventh day of culture, analyzed for phenotypic markers by flow cytometry and used in functional studies.

To analyze DC for cell surface marker expression by flow cytometry, standard methods were employed. Briefly, the cells were aliquotted into polystyrene tubes and stained for surface markers with fluorochrome-labeled murine antibodies. The complete DC cell surface marker panel included: HLA-A, HLA-A B, HLA-A C, HLA-DR, CD 14, CD11c, CD123, CD4, CD40, CD83, CD86, CD80, CD16, CD32, CD64 (specific detectably labeled antibodies to which are commercially available from Becton Dickinson, San Jose, Calif.). Following a 30 min. incubation on ice, the cells were washed with PBS and pelleted by centrifugation. The cell pellets were resuspended in 250 μl of fixative (2% paraformaldehyde). The data was acquired using a FACS-Can flow cytometer (Becton Dickinson, San Jose, Calif.) and analyzed with Cellquest software (Becton-Dickinson, San Jose, Calif.).

Example II

Phenotypic Markers on Dendritic Cells

Initial studies were focused on the uptake of CA125 in monocytes and dendritic cells in the presence or absence of Alt-2. For this purpose, CA125 was purified from tissue culture supernatant of NIH:OVCAR-3 cells (AltaRex Corp.). Highly purified CA 125 was labeled with Fluorescein (Flourescein-EX, Molecular Probes), and incubated with monocytes, immature dendritic cells, and mature dendritic cells under various conditions. In some experiments, the uptake of MAb-Alt-2 was also followed, where the MAb-Alt-2 was labeled with Fluorescein-EX or Cy-3.

As shown above in Table I, monocytes, immature DC, and mature DC could be easily distinguished based on their expression of various cell surface antigens.

Example III

Comparison of CA125 Antigen Uptake in Monocytes to Immature Dendritic Cells

Figure 1A:
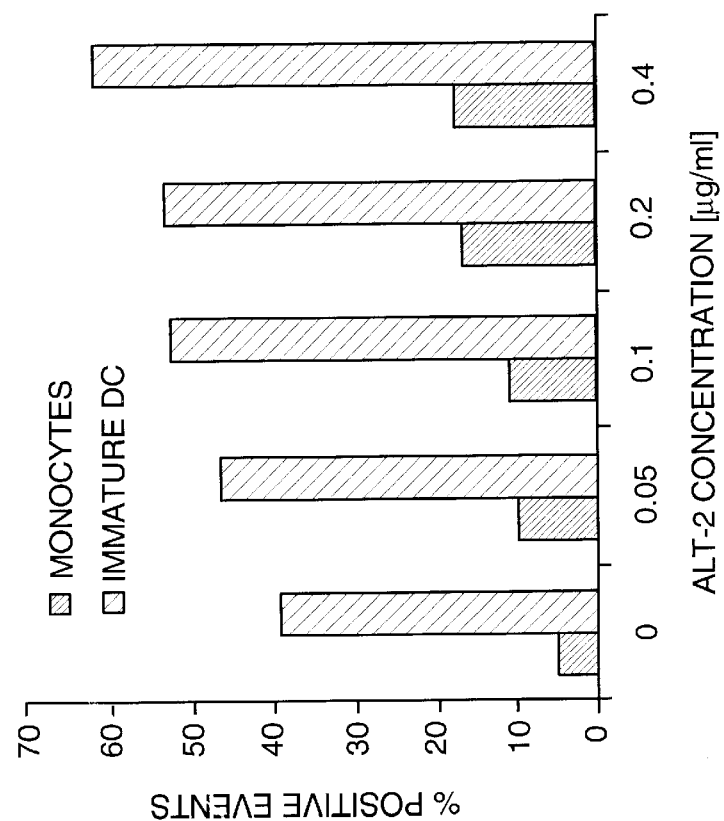

In these studies, highly purified CA125 was labeled with Fluorescein and incubated with monocytes or immature dendritic cells at 1000 U/mL for 1 hour at 37° C. In some cases, unlabeled antibody was added simultaneously with the labeled antigen to study the effect of complex formation on the uptake by the two antigen-presenting cells. The binding to cells was quantified by flow cytometry and the results are shown in FIGS. 1A (percent positive events) and 1B (mean channel intensity). As shown in FIGS. 1A and 1B, immature dendritic cells showed much higher uptake of the antigen, with MAb Alt-2 as compared to without MAb Alt-2. Both monocytes and immature dendritic cells showed an increase of CA125 uptake in the presence of MAb Alt-2 (see FIGS. 1A and 1B, respectively). For the immature dendritic cells, the CA125 concentration needed to be lowered to 1000 U/mL to allow the detection of an antibody effect (concentration below the saturation point for CA125 uptake).

It is interesting to note that immature DCs showed an increase in the number of cells capable of taking up the CA125 antigen (FIG. 1A, % positive cells) as well as the concentration of antigen within each cell (FIG. 1B, mean fluorescence intensity) with increasing concentrations of MAb Alt-2. In monocytes, increasing antibody concentrations could only enhance the percentage of cells capable of taking up the CA 125 antigen. These results may indicate that the immune complexes are either taken up by different receptors in monocytes and immature DCs or that the immune complexes are taken up by the same receptors in monocytes and immature DCs, but the receptor is recycled at a higher frequency in immature DCs. The receptor is certainly more abundant and/or is internalized more rapidly in immature DCs than monocytes, demonstrated by the higher percentage of targeted cells in DCs (see FIG. 1A).

Figure 2:
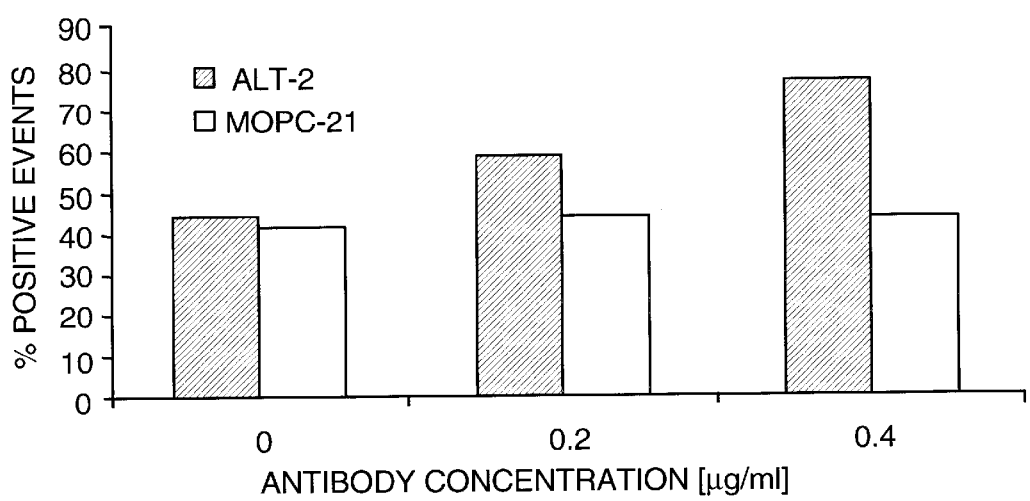
FIG. 2 is a bar graph showing the uptake of 1000 U/ml FITC-labeled CA125 antigen in the presence of 0, 0.2, or 0.4 µg/ml Alt-2 antibody or control MOPC-21 antibody

Next, the requirement for antibody specificity was tested. To do this, highly purified CA125 was labeled with Fluorescein and incubated with immature dendritic cells at 1000 U/mL for 1 hour at 37° C. in the absence and presence of unlabeled MAb Alt-2 or MOPC-21 (a control murine IgG1 that does not bind to the CA125 antigen). The binding to cells was assessed by flow cytometry, and the results are shown in FIG. 2. As FIG. 2 shows, antibody-enhanced uptake of CA125 was specific for MAb Alt-2 and could not be achieved with a control antibody that does not bind to CA125. Consequently, the antibody-enhanced uptake is due to a more efficient uptake route in DCs and not due to stimulation of the endocytotic activity of dendritic cells upon receptor engagement by the binding MOPC-21 antibody Example IV Effect of Murine Alt-2 and Chimeric Alt-2 on CA125 Antigen Uptake Other binding studies have compared the uptake of CA125 in the presence of a murine and humanized form of MAb Alt-2. In this study, fluorescein-labeled CA125 was incubated with monocytes and immature DCs at 1000 U/mL for 1 h at 37° C. in the presence of murine (mAlt-2) and chimeric Alt-2 (cAlt-2 (chimeric with a human IgG3 constant region)). The binding to cells was assessed by flow cytometry.

Figure 3A:
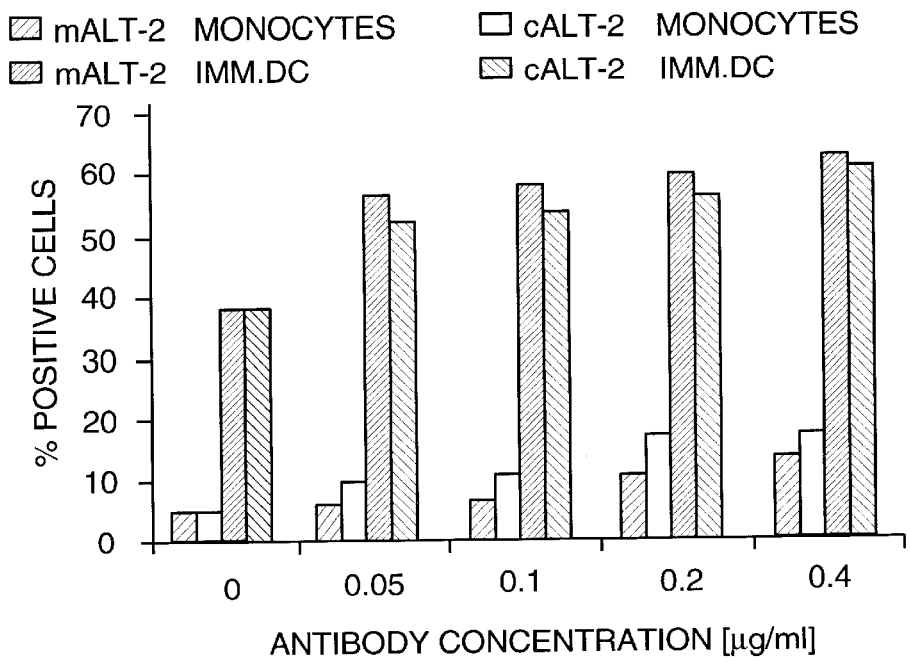
FIGS. 3A and 3B are bar graphs showing the percentage of positive events (FIG. 3A) and mean channel intensity (FIG. 3B) of monocytes or immature dendritic cells incubated with 1000 U/ml FITC-labeled CA125 antigen and the indicated amounts of murine Alt-2 or chimeric Alt-2.
Figure 3B:
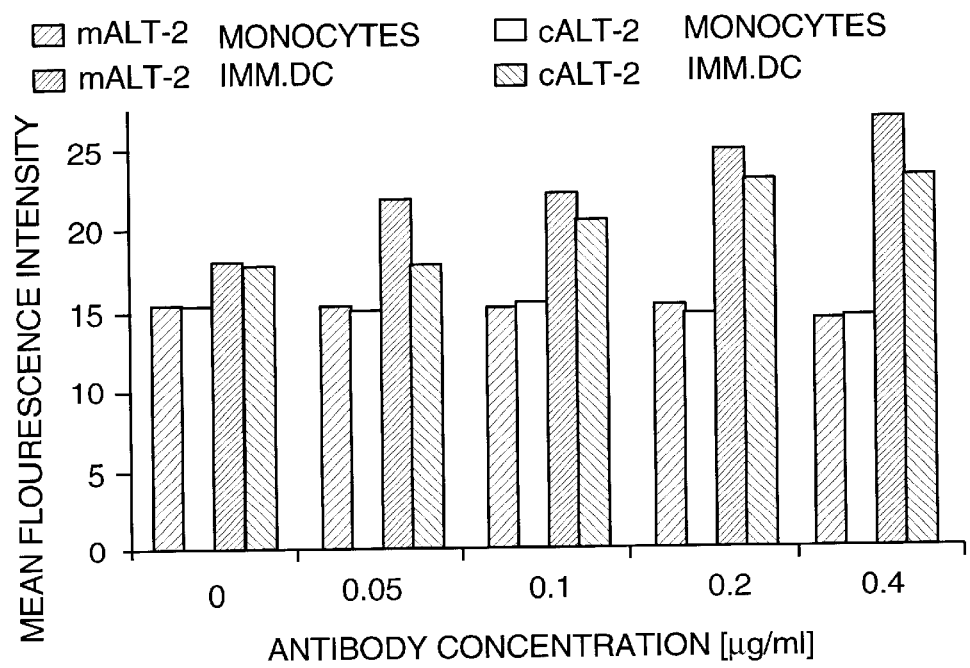

As shown in FIGS. 3A and 3B, the chimeric antibody showed slightly better enhancement of CA125 binding to monocytes than the murine Alt-2; on immature dendritic cells, the murine and chimeric antibody were equally effective. As for the murine antibody, the chimeric Alt-2 increased the percentage of CA125-targeted cells within the monocytes (FIG. 3A) and dendritic cell populations, but increased the amount of CA125 per cell only in dendritic cells (FIG. 3B).

Example V

Effect of HAMA on CA125 Antigen Uptake

Complexation of antibody with specific antigen or with HAMA and binding to dendritic cells was measured. To do this, human anti-mouse antibody (HAMA) was purified from patient serum samples with high HAMA concentrations after MAb Alt-2 injection via affinity chromatography on Protein G, and a MAb-AR20.5 column, followed by negative selection on a MAb Alt-2 column to eliminate Ab2 (i.e., human antibody that binds to the idiotype of the MAb Alt-2 antibody).

Figure 4A:
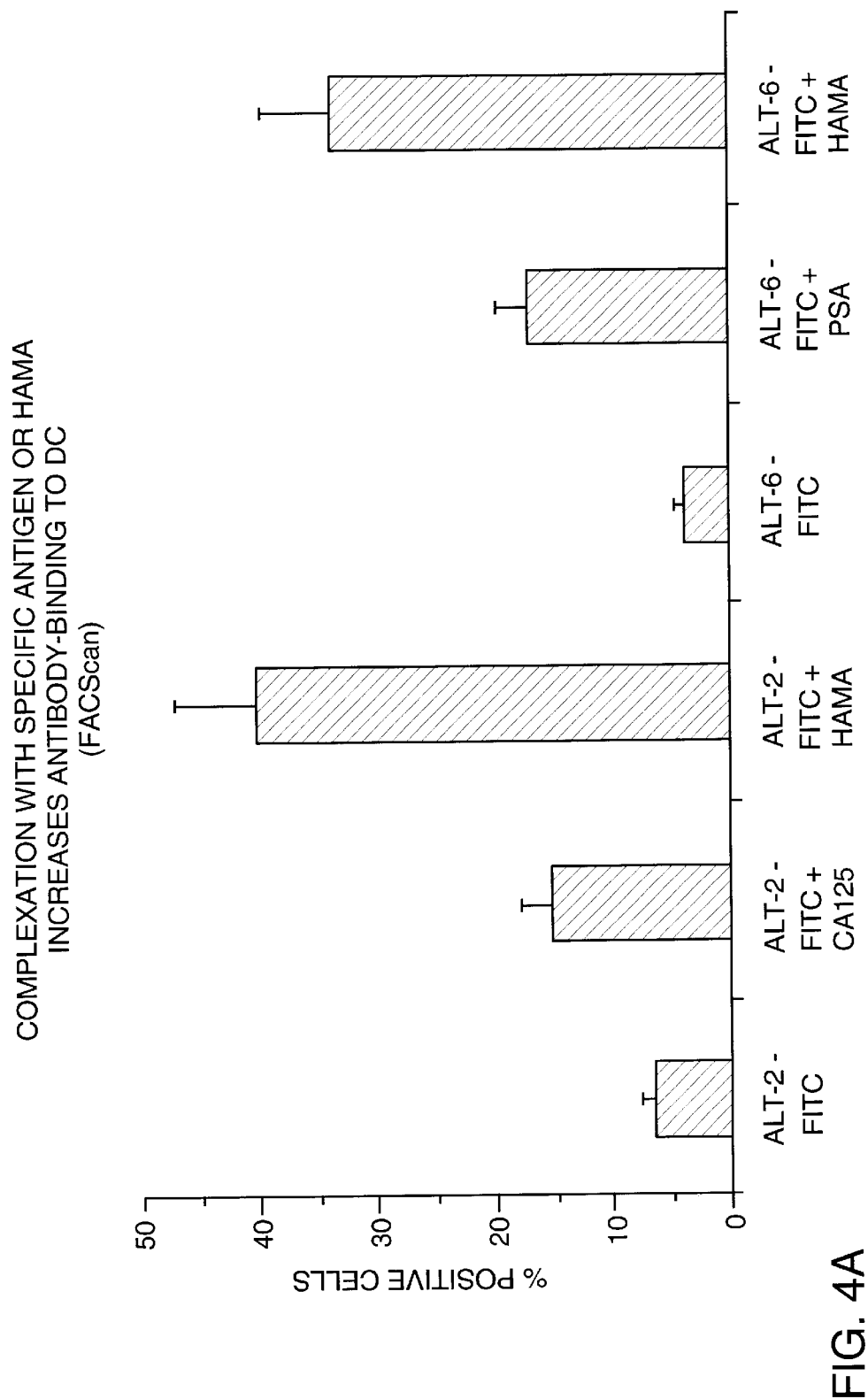
FIGS. 4A, 4B and 4C are bar graphs showing the effect of complexation with HAMA (FIG. 4A), specific antigen (FIGS. 4A and 4B), or both (FIG. 4C) on antibody binding to dendritic cells.
Figure 4B:
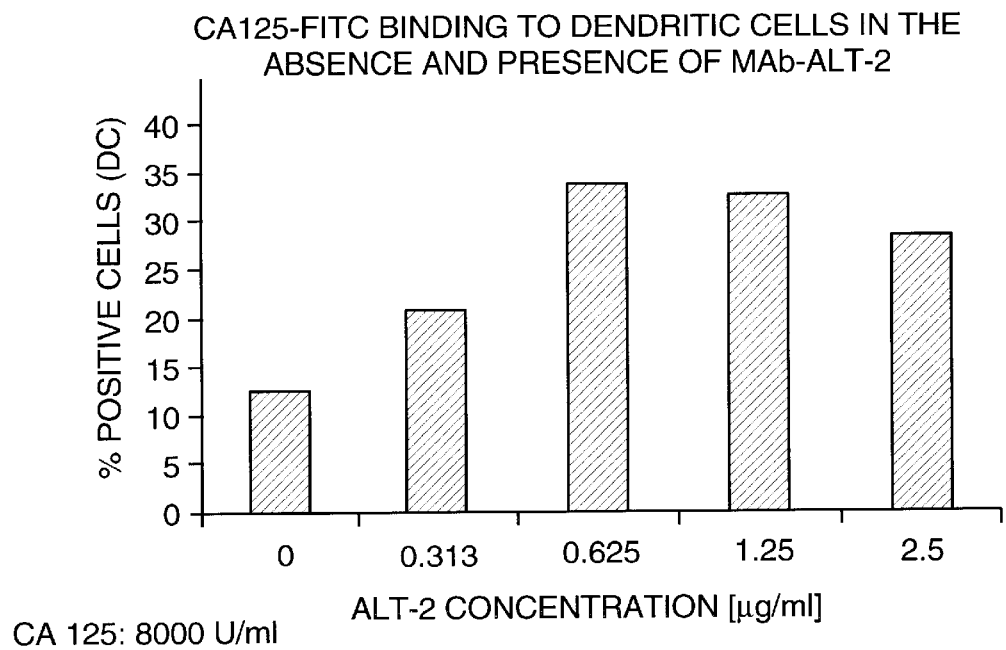
Figure 4C:
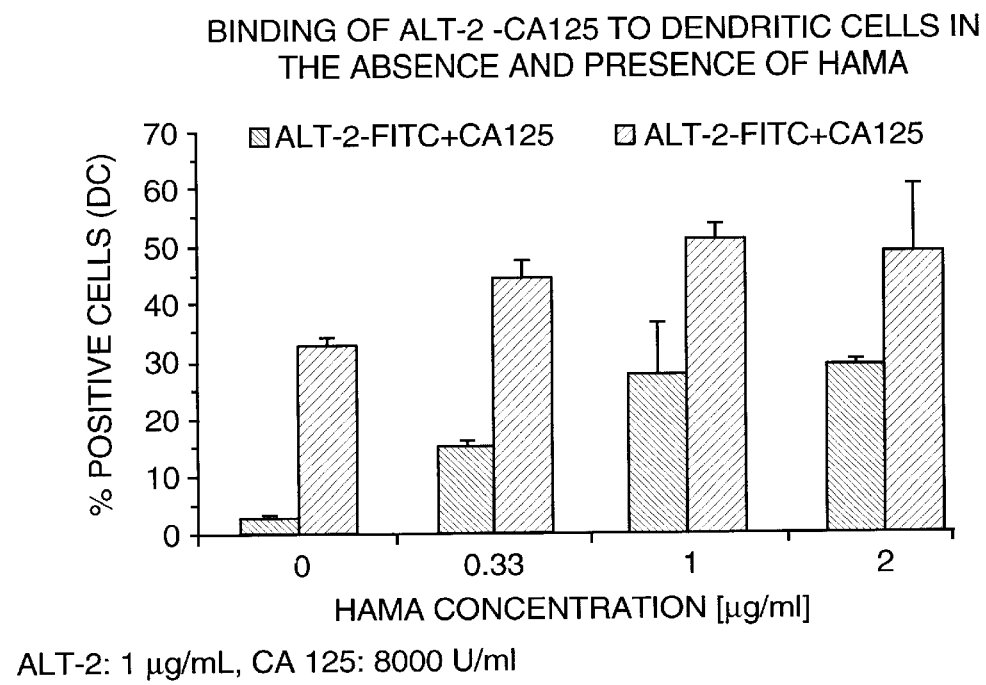

Five micrograms (5 µg) FITC-labeled Alt2 (anti-CA125) or Alt-6 (anti-PSA) murine monoclonal antibody was incubated together with the corresponding antigen (1 µg) and/or HAMA (2.5 µg) and $5 \times 10^5$ dendritic cells at 37° C. for 60 minutes. The mixture was then washed once and resuspended in 0.5% formalin+PBS and subjected to FACScan on a FACSCalibur machine (Beckton-Dickinson). The results for Alt-2 and CA125 are shown in FIGS. 4A, 4B, and 4C. These results demonstrate that binding of antibody to dendritic cells is enhanced by complexation of antibody to its antigen, complexation of antibody with HAMA, or complexation of antibody to its antigen in the presence of HAMA.

Further binding studies were conducted to compare the uptake of the CA125-MAb-Alt-2 complex by monocytes or immature dendritic cells in the presence and absence of HAMA. In this study, fluorescein-labeled CA125+murine MAb-Alt-2 was incubated at 1000 U/ml of CA125 and a range of MAb-Alt-2 concentrations with monocytes or immature dendritic cells for 1 hour at 37° C. The binding studies were conducted in the absence and presence of human anti-mouse antibodies (HAMA). The HAMA concentrations were equivalent to the MAb-Alt-2 concentrations to form equimolar complexes of HAMA and MAb-Alt-2. The binding to cells was assessed by flow cytometry.

Figure 5A:
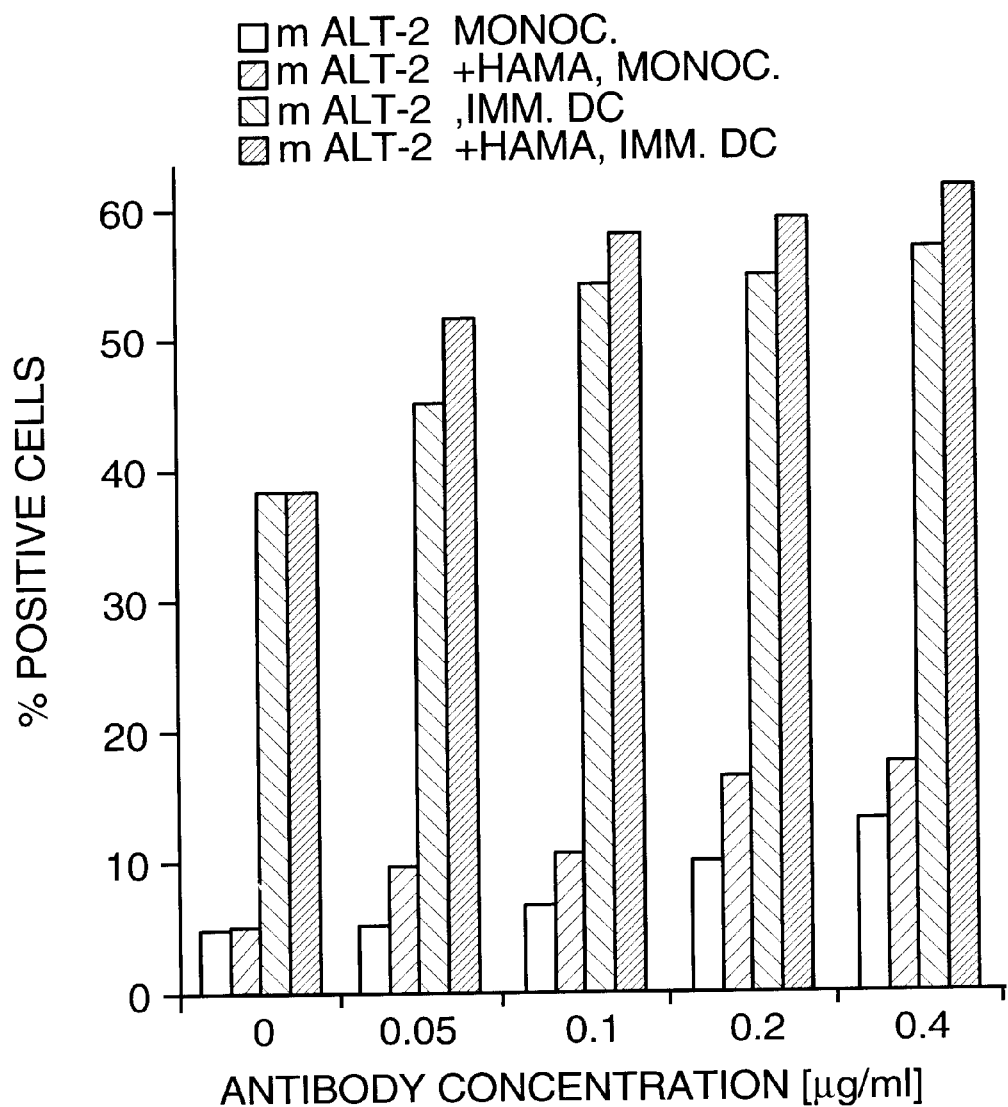
FIGS. 5A and 5B are bar graphs showing the uptake of CA125-Alt-2 immune complexes in monocytes and immature dendritic cells in the presence and absence of HAMA as measured by the percentage of positive events (FIG. 5A) and mean channel intensity (FIG. 5B) for monocytes or immature dendritic cells.
Figure 5B:
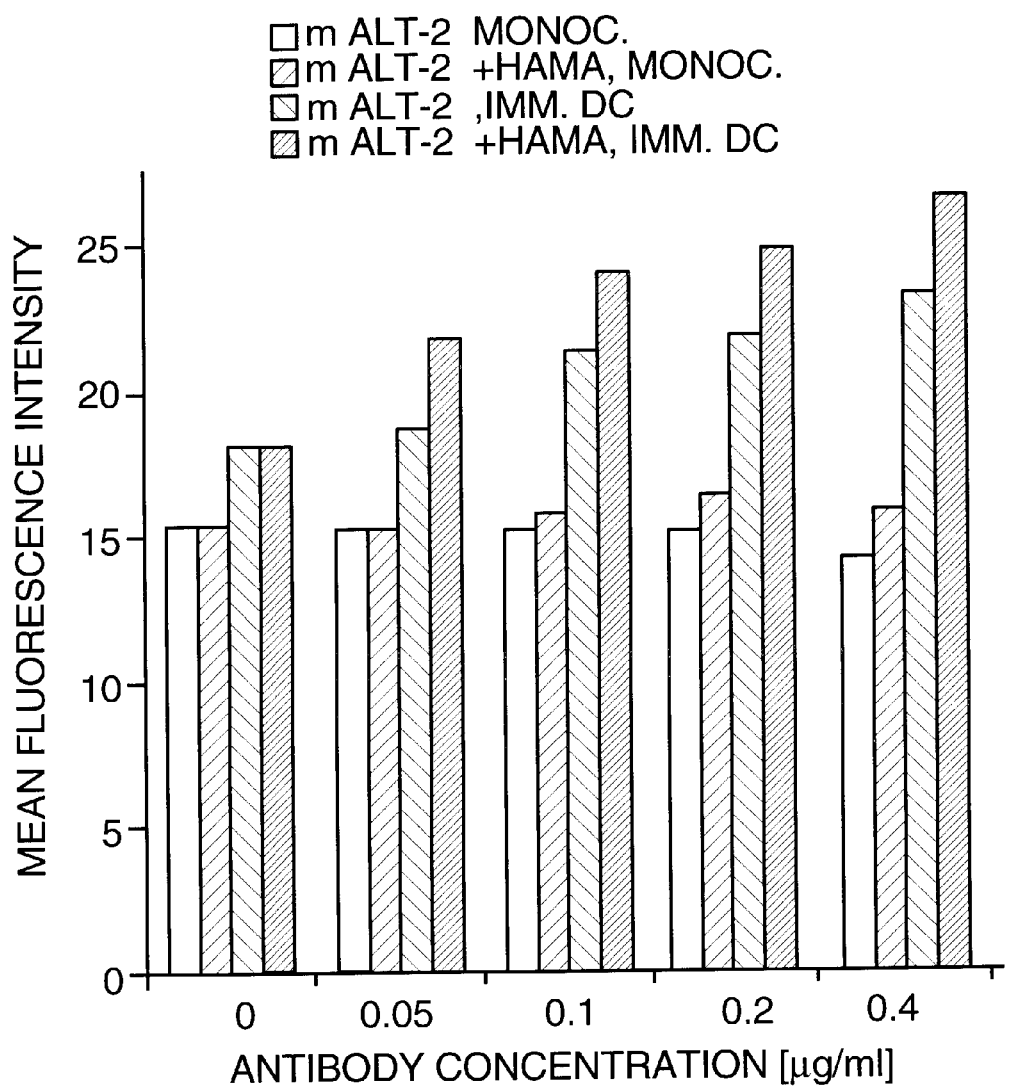

As shown in FIGS. 5A (percent positive cells) and 5B (mean fluorescence intensity), HAMA further enhanced the binding of CA125 to human monocytes and dendritic cells. Immune complexes with HAMA increased the percentage of CA125-targeted cells within the monocytes and dendritic cell populations (FIG. 5A), but increased the CA125 concentration per cell mainly in dendritic cells (FIG. 5B).

Example VI

Alt-6 Antibody and Alt-6-PSA Immune Complex Binding to DC at Different Stages of Development and Maturation DC of different stages of development and maturation were first analyzed by flow cytometry to determine their level of expression of Fcγ receptor. To do this, DC were isolated from PBMC as described above and tested for Fcγ receptor expression with fluorescence labeled antibodies at day 0, after 4 days in culture with GM-CSF/IL-4 and after maturation with TNFα and IFNα (7 days). Binding was determined on CD11c+, HLA-DR+ cells and is expressed in Table II (below) as percentage of positive cells within the gate.

As shown below on Table II, DC express Fcγ type I, and type II receptors (CD64 and CD32), and low levels of FcγR III (CD16)

TABLE II

Distribution of Fcγ Receptors on DC at Different Stages of Maturation

| | Days in culture | | |
|---|---|---|---|
| | 0 | 4 | 7 |
| Fcγ Receptor | Positive Cells [%] (gated on DC) | | |
| CD16 (FcγRIII) | 3–15 | 15–40 | 0.5–5 |
| CD32 (FcγRII) | 89–98 | 70–95 | 40–45 |
| CD64 (FcγRI) | 92–99 | 28–60 | 4–10 |

The percent of DC expressing these Fcγ receptors differed depending on their stage of maturation/differentiation. As shown on Table II, the number of DC expressing CD16 was highest after culture for 4 days with GM-CSF/IL-4 and was nearly absent on DC after maturation (i.e., after 7 days in culture with GM-CSF/IL-4). CD32 and CD64 were found on the majority of DC precursors. CD32 was expressed on 70–95% of immature DC and declined to about 40% on mature DC. In addition, the number of CD64 expressing cells declined as the DC differentiated and matured.

Next, to determine if the anti-PSA monoclonal antibody Alt-6 and Alt-6-PSA immune complexes would bind to DC and if the stage of DC differentiation and maturation affected binding, a range of concentrations of the fluorescein-labeled Alt-6 as well as Alt-6-PSA-FITC-complexes were added to three different populations of DC: I) freshly isolated myloid DC precursors (surface phenotype-CD11c+, HLA-DR+, CD14+), II) DC after culture for 4 days in GM-CSF/IL-4 (surface phenotype-CD11c+, HLA-DR+, CD14−, CD86+) and III) DC that had been further matured by culturing for an additional 3 days with TNFα and IFNα (surface phenotype-CD11c+, HLA-DR+, CD86+, CD40+, CD80+, CD83+) (see Table I above).

To do this, PSA was purchased from Scripps Laboratories (San Diego, Calif.) and the murine monoclonal anti-PSA antibody Alt-6 (ProstaRex™) was kindly provided by AltaRex Corporation, Edmonton, Alberta, Canada (ATCC No. HB-12526; American Type Culture Collection, Manassas, Va.). Alt-6 is an IgG1 antibody that reacts specifically with an epitope that maps to the region of amino acid residues 137–146 (sequence EPEEFLTPKK (SEQ ID NO:1)) of PSA. PSA and Alt-6 were diluted in cRPMI to concentrations of 5 and 25 µg/m, respectively. When mixed at these concentrations, approximate equimolar amounts of PSA and anti-PSA were achieved.

Alt-6 was labeled with Fluorescein-EX (commercially available from Molecular Probes, Eugene, Oreg.) following manufacturers instructions. Equimolar concentrations of PSA were mixed with 1.25 µg/ml, 2.5 µg/ml, 5.0 µg/ml, and 25 µg/ml of Alt-6-FITC and added to freshly isolated DC precursors, to DC that had been cultured for 4 days in the presence of GM-CSF/IL-4 and to DC that had been matured.

The antibody-PSA composition was incubated for 1 hour at 37° C., washed, pelleted, fixed in 2% paraformaldehyde, and analyzed by flow cytometry. DC were gated in the sideward/forward scatter based on DC preparations stained in parallel with the complete DC marker panel (see Example I). The percentage of cells that reacted with Alt-6 and Alt-6-PSA complexes were calculated based on binding to CD11c+, HLA-DR+ cells. Table III (below) shows percentage of positive cells within the gate.

TABLE III

PSA-Specific Monoclonal Antibody Alt-6 and Alt-6-PSA Immune Complex Binding to DC at Different Stages of Maturation

| | | Days in culture | | |
|---|---|---|---|---|
| | Antibody Concentration | 0 | 4 | 7 |
| | | Positive Cells (gated on DC) [%] | | |
| Alt-6-FITC | 1.25 µg/ml | 0.13 | 0.68 | |
| | 2.5 µg/ml | 0.16 | 1.56 | |
| | 5 µg/ml | 1.84 | 9.95 | 1.19 |
| | 25 µg/ml | 7.33 | 28.1 | |
| Alt-6-FITC + PSA | 1.25 µg/ml | 1.82 | 2.41 | |
| | 2.5 µg/ml | 3.91 | 8.70 | |
| | 5 µg/ml | 5.38 | 23.40 | 1.56 |
| | 25 µg/ml | 18.00 | 72.11 | |

As shown in Table III, at the concentrations tested, Alt-6 bound to a low percentage of freshly isolated DC precursors. The number of cells binding the antibody increased after culture for 4 days in GM-CSF and IL-4. Interestingly, the number of cells binding Alt-6-FITC was significantly higher in the presence of PSA, indicating that the Fc receptors have enhanced binding to immune complexed antibody over the antibody alone, or that immune complexes bind to different and/or more abundant receptors on DC precursors and immature DC. No binding of the Alt-6 or the immune complexes occurred to mature DC.

Example VII

T Lymphocyte Responses to DC Armed With PSA or PSA/Anti-PSA

T lymphocytes were stimulated with DC armed with PSA or a combination of PSA/anti-PSA antibody.

To do this, monocytes were generated from leukaphoresis samples from healthy donors (Biological Specialty Corp., Colmar, Pa.) and depleted from lineage cells by incubation with anti-CD3, CD19 and CD 16 antibodies, followed by incubation with magnetic bead conjugated anti-mouse Ig and separation on a magnet (Dynal). Negatively selected cells were approximately 70% pure monocytes as characterized by flow cytometry using a broad CD marker panel (see Example 1). Monocytes were incubated with IL-4 and GM-CSF (R&D Systems) for 4 days in RPMI1640+10% matched human serum to generate immature DC. Again, an aliquot of the cells was stained with a broad CD marker panel to ensure purity and identity of the cells. These cells were then harvested and loaded with antigen combinations (e.g., PSA, the anti-PSA monoclonal antibody and the antibody-PSA combination) for 2–8 hours at 37° C., and then matured with IFN-α and TNF-α for three days. Dendritic cell were checked again via flow cytometry for an array of CD markers to ensure proper maturation of the cells.

Specifically, the immature DCs were loaded with PSA (25 µg/mL), Alt-6 (5 µg/mL) and PSA+Alt-6 (25 µg/L of PSA; 5 µg/mL of Alt-6). These immature DCs were added to T cells that were generated from the same monocytes as the DCs via negative selection (i.e., autologous T cells), using a magnetic T cell isolation kit (commercially available from Dynal). Briefly, to isolate T cells, CD3+ T lymphocytes were isolated from thawed PBMC (see Example I) by negative selection (using magnetic beads commercially available from Dynal, Lake Success, N.Y.). Briefly, the cells were incubated on ice for 30 min with a mixture of antibodies to CD14, CD16, CD56 and HLA Class II DR/DP. Excess antibodies were removed by washing with PBS/0.1% BSA. The cells were incubated for 30 min. at room temperature with immunomagnetic beads coated with an anti-mouse IgG antibody (Dynal). The cells were placed against a magnet and the T lymphocytes, which did not bind the magnet (i.e, did not express CD14, CD16, CD56, and HLA class II DR/DP) were isolated from the supernatant.

T cells and DCs were incubated for 7 days (primary stimulation), re-stimulated with loaded and matured DCs and incubated for another 7 days. For stimulation, T lymphocytes were plated in twenty-four well plates at a concentration of $1\times10^6$ cells/well and to which were added $5\times10^4$ DC that were antigen naive or that had been exposed to PSA, the anti-PSA monoclonal antibody or the combination of PSA and the monoclonal antibody. An aliquot of the cells was taken 24 hour later and prepared for intracellular cytokine staining (Day 15; primary stimulation), whereas the remaining cells were incubated for another 7 days (secondary stimulation) and prepared for intracellular cytokine staining on Day 22. Prior to adding the second or third DC preparation, an aliquot of the cell supernatant was taken for testing in an IFN-γ ELISA (Pharmingen DouSet).

For the intracellular cytokine staining, cells were incubated with Golgi Plug (R&D Systems) 2 hours after DC addition and incubated for another 16–18 h. Cells were stained with anti-CD3-FITC and anti-CD8-Cy-Chrome for 30 min. on ice, washed, permeabilized, and stained with anti-IFN-γ-PE for 30 min. on ice. Cells were washed, fixed and analyzed by flow cytometry (FACS Calibur, Becton Dickinson).

T cell responses were measured as numbers of CD4+ and CD8+ T cells producing intracellular IFNγ. To do this, flow cytometry was used. Briefly, Brefeldin A (10 μg/ml) (commercially available from Pharmingen, San Diego, Calif.) or Golgi Plug (commercially available from R&D Systems) was added to the T cell cultures 2 hours after restimulation with antigen armed DC. After an additional 16–18 hours of culture, cells were stained with anti-CD3-FITC and anti-CD8-Cytochrome for 30 min. on ice, washed, permeabilized (e.g., by incubating in a perm/fix solution (Pharmingen) for 20 min. on ice), and stained with anti-IFN-γ-PE for 30 min. on ice in staining buffer (PBS with 1% human AB serum (i.e., human sera from a person with type AB blood) (antibodies commercially available from Becton Dickinson, San Jose, Calif.) added. The cells were washed, resuspended in staining buffer containing 2% paraformaldehyde and analyzed by flow cytometry (FACS Calibur, Becton Dickinson).

In this experiment, mature "armed" or "un-armed" DC (i.e., matured with cytokines alone) were co-cultured with autologous T cells, restimulated with armed or un-armed DC, and the number of CD4+ and CD8+ cells producing IFNγ was determined. The results of a representative experiment are shown in FIG. 6.

As shown in FIG. 6, little to no difference in number of IFNγ producing CD4+ or CD8+ T cells were found in co-cultures with DC that were not exposed to antigen (negative control) or T cells cultured with DC that had been exposed to the monoclonal antibody (i.e., α-PSA as primary stimulated) and were then restimulated with armed or un-armed DC. In all combinations of primary stimulation and restimulation, PSA armed DC stimulated CD4+ T cell responses were consistently greater than CD8+ T cell responses. Notably, strong CD8+ T cell responses were observed on restimulation with immune complex armed DC (i.e., where restimuation was with the complex and primary stimulation was with the complex of PSA/α-PSA). When T cells were cultured with antigen-antibody armed DC (i.e., primary stimulation is PSA/α-PSA) and restimulated with PSA armed DC, CD4+ T cell responses were substantially greater than CD8+ responses.

On the other hand, consistent CD4+and CD8+IFNγ responses were only generated in T cells exposed to and restimulated by antigen-antibody armed DC (i.e., where both primary stimulation and restimulation was PSA/α-PSA). Since IFNγT cell responses were not generated to the Alt-6 antibody (i.e., α-PSA alone as primary stimulation or restimulation), it is expected that the response to the complex is directed at the PSA. The increase in CD8+ T cell responses to PSA presented in combination with the antibody compared to the responses with free PSA alone indicate that the immune complex enhances antigen processing, in particular, through the HLA Class I pathways.

Example VIII

T Lymphocyte Responses to DC Armed With CA125 or CA125/αCA125 Complex

After identifying broad ranges of functional CA125 and MAb-Alt-2 concentrations for T cell stimulation in small checkerboard assay for IFN-γ release into the supernatant, intracellular cytokine staining assays were performed using 50, 500 and 5000 U/mL of CA125 in the absence and presence of 2.5 μg of MAb-Alt-2. Matured DC cells and T cells were incubated for 7 days and then re-stimulated with loaded and matured DCs. Seven days after stimulation with loaded DCs (FIG. 7, round 1), and after the restimulation (FIG. 7, round 2), an aliquot of the cell supernatant was taken and tested in an IFN-γELISA (Pharmingen DouSet).

As a positive control, PMA+Ionomycin was used for stimulation of the T cells in culture. DCs loaded in medium only were used to determine the background of the assay.

Figure 7:
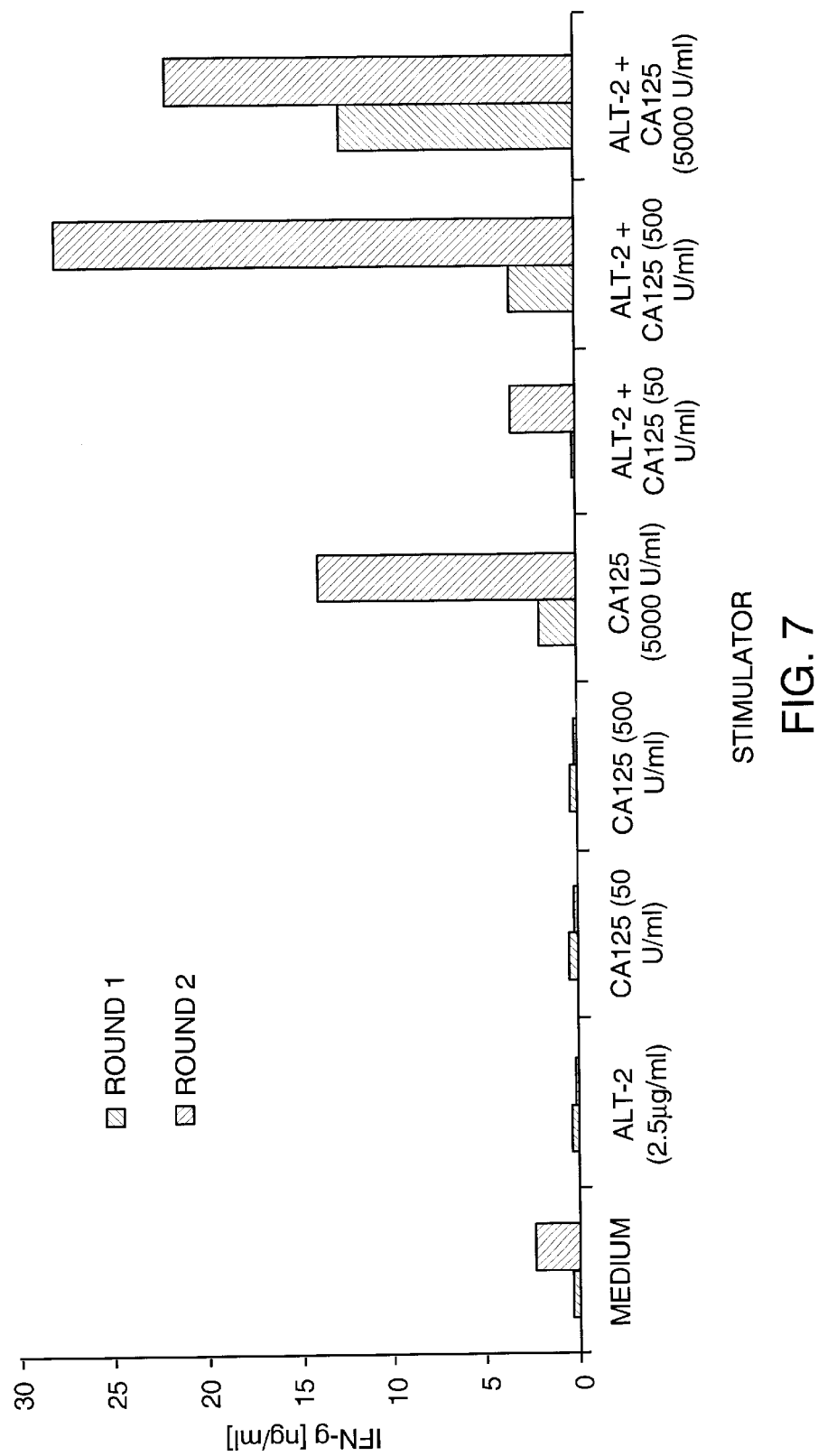
FIG. 7 is a bar graph showing IFN-γ release from T cells stimulated with DC loaded with CA125, Alt-2, or CA125/Alt-2 complex (i.e., CA125/αCA125 complex) at the indicated concentrations for a seven day incubation period (round 1) or for an initial seven days and an additional seven days with freshly loaded DCs (round 2).

As shown on FIG. 7, stimulation with CA125 alone did not result in substantial IFN-γ release, detected by IFN-γ ELISA of the cell supernatants (FIG. 7).

Figure 8A:
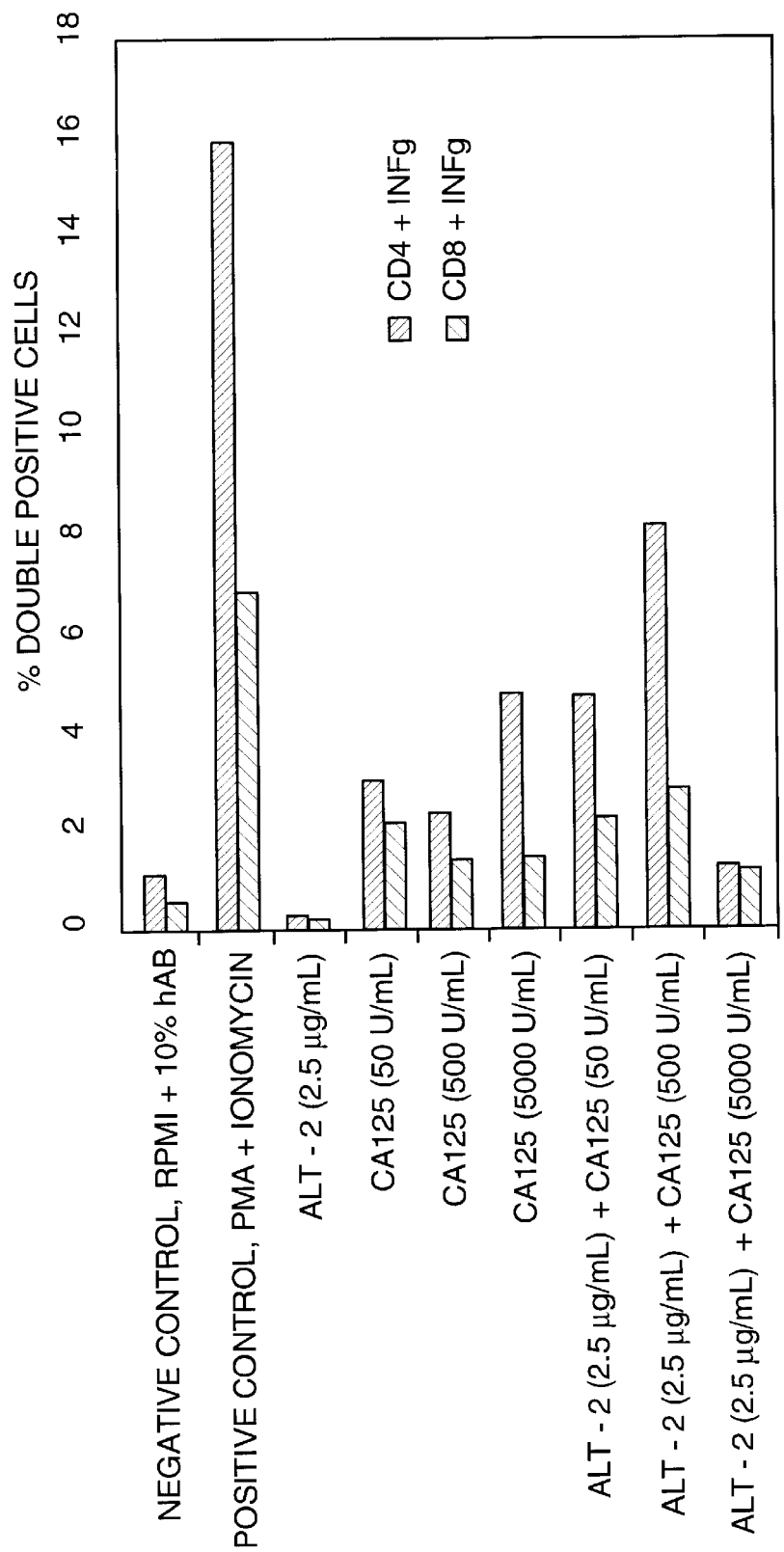
FIGS. 8A and 8B are bar graphs showing intracellular IFN-γ production from CD4α T cells or CD8+ T cells stimulated with DC loaded with CA125, Alt-2, or CA125-Alt-2 complex (i.e., CA125/αCA125 complex) at the indicated concentrations for a seven day incubation period (FIG. 8A) or for an initial seven days and an additional seven days with freshly loaded DCs (FIG. 8B).
Figure 8B:
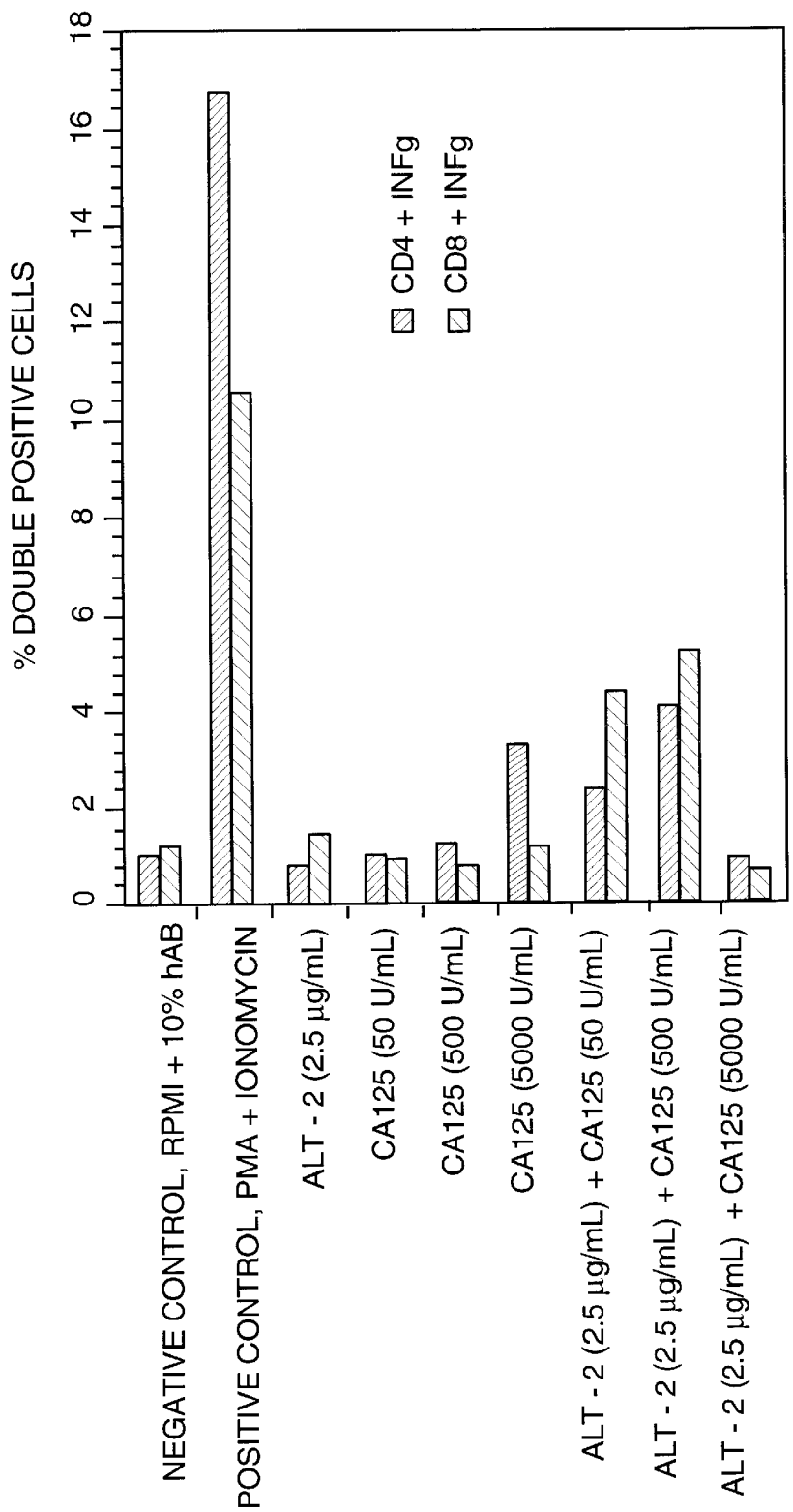

For intracellular staining studies, immature DCs were loaded with CA125 (50, 500, 5000 U/mL), Alt-2 (2.5 μg/mL) and CA125+Alt-2 (50, 500, 5000 U/mL of CA125; 2.5 μg/ml of Alt-2) and matured. T cells and DCs were incubated for 7 days, and re-stimulated with loaded and matured DCs. An aliquot of the cells was taken 24 hours later and prepared for intracellular cytokine staining (Day 15; FIG. 8A), whereas the remaining cells were incubated for another 7 days. Those cells were stimulated with another batch of loaded and matured DCs and prepared for intracellular cytokine staining on Day 22 (FIG. 8B). For the intracellular cytokine staining, cells were incubated with Golgi Plug (R&D Systems) 2 hours after DC addition and incubated for another 16–18 hours. Cells were stained with anti-CD3-FITC and anti-CD8-Cy-Chrome for 30 min. on ice, washed, permeabilized, and stained with anti-IFN-γ-PE for 30 min. on ice. Cells were washed, fixed and analyzed by flow cytometry (FACS Calibur, Becton Dickinson).

As shown on FIGS. 7, 8A, and 8B, responses to CA125 could be detected only after two stimulation rounds and at the highest concentration tested. As shown in FIGS. 8A and 8B, antigen alone mainly stimulated CD4 responses as shown by the intracellular staining results. As shown on FIG. 7, substantially increased IFN-γ release was observed in responses to CA125 presented in a complex with MAb-Alt-2 by human DC. IFN-γ release into the cell supernatant, detected by IFN-γ ELISA, as well as intracellular cytokine production (ICC) could be detected already after one stimulation round and was further increased after the second round of stimulation (FIGS. 7 and 8B, respectively). CA125 concentrations as low as 50 U/mL were able to stimulate T cells, with an optimum of 500 U/mL at two stimulation rounds (FIGS. 7, 8A, and 8B).

Of particular note is the finding that the CA125-MAb Alt-2 immune complexes induced initially strong CD4 responses (FIG. 8A) and with additional stimulation also strong CD8 responses (FIG. 8B). These observations indicate that CA125 can be presented on MHC class I and II if presented in the form of an immune complex, but only on MHC class II molecules, if taken up alone, as expected for extracellular antigens. The receptor responsible for the uptake of the antigen or antibody-antigen complex may influence the route for processing of the internalized protein. Antigen-antibody complexes may have increased leakage into the cytosol and therefore better chance of being processed by the proteasomes, the processing machinery that transports peptides onto MHC class I molecules via the invariant chain.

Example IX

PSA/Anti-PSA Complex-Armed DC Generate HLA-A*0201 Peptide-Specific T Lymphocyte Responses The ability of PSA/anti-PSA immune complexes and PSA armed DC to generate T lymphocyte responses to two PSA peptides that are known to be restricted by the HLA-A*0201 allele was next compared. To do this, two HLA-A2 specific PSA peptides (pep 1, FLTPKKLQCV, SEQ ID NO: 2; pep 2, KLQCVDLHV, SEQ ID NO: 3) and an HIV-1 peptide (SYNTVAVL, SEQ ID NO: 4) were synthesized by the Biopolymer Laboratory, University of Maryland, Baltimore, Md., diluted in cRPMI, added to the DC preparations at concentrations of 5 µg/ml, and incubated for approximately 1 hour.

DC were prepared as described in Example I and exposed to PSA or PSA/anti-PSA complex after 4 days of culture in GM-CSF/IL-4. Following maturation with CD40L or TNFα and IFNα, the armed DC were cultured with autologous CD3+selected T lymphocytes for 7 days. The T cells were next harvested, newly armed DC added to the cell culture, and the cells cultured for an additional 7 days in media supplemented with IL-2 (10 U/ml) and IL-7 (5 ng/ml) (see Example III).

At day 14, the T cells were harvested and restimulated with matured DC that were pulsed with the two PSA-derived peptides and analyzed for IFNγ release.

Figure 9:
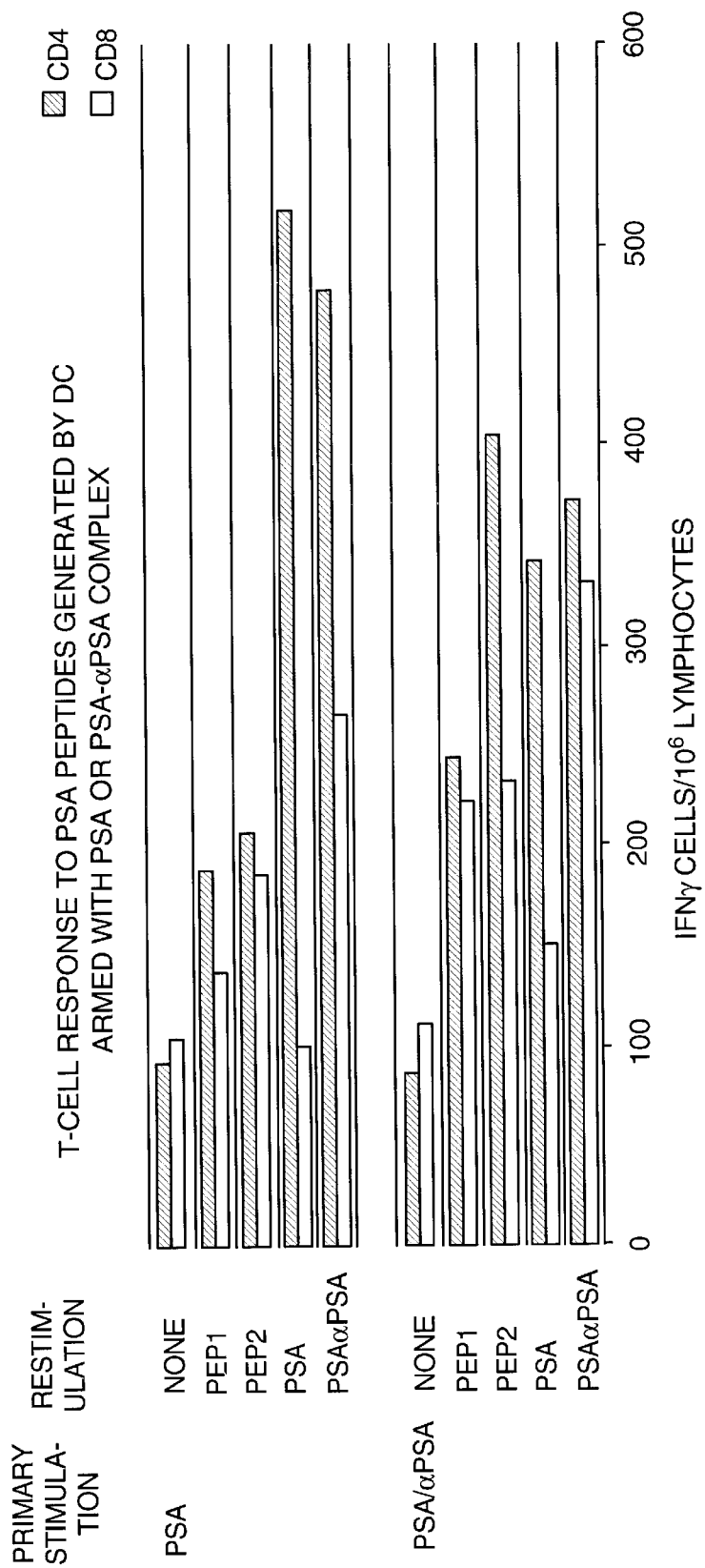
FIG. 9 is a bar graph showing the in vitro T cell activation (both CD4+ and CD8+ T cells) to peptides generated by dendritic cells "armed" by the indicated primary stimulation and restimulation. T cell activation was determined by the number of IFNγ producing cells per $10^6$ cells.

Results of a representative experiment (1 of 3) are shown in FIG. 9. In T cells cultured with PSA-armed DC for 2 weeks, low levels of CD4+ responses were detected upon restimulation with the PSA-derived peptides. Peptide 2 (KLQCVDLHV) (SEQ ID NO:3) also induced small CD8+ responses when the primary stimulation was PSA alone. Consistent with the previous results described in Example III, restimulation of T cells with PSA-armed DC (where the primary stimulation was PSA) resulted in CD4+T cell responses, and low levels of responding CD8+T cells. Restimulation with the PSA/anti-PSA complex (where the primary stimulation was PSA) showed similar activation of CD4+T as well as CD8+INFγ responses.

As the lower half of FIG. 9 shows, T cells cultured with PSA/anti-PSA armed DC for two weeks were able to respond to both PSA-derived peptides. Peptide-restricted responses were approximately twice as strong in T cells cultured with PSA/anti-PSA armed DC before restimulation as compared to the responses to peptide by PSA-armed DC (i.e., T cells whose primary stimulation was PSA alone).

Note that T cells propagated in the presence of PSA-armed DC were able to respond weakly to peptide 2 (KLQCVDLHV) (SEQ ID NO:3), but the CD8+T cells did not release IFNy upon restimulation with PSA-armed DC. This result suggests that this peptide may be presented by HLA Class II molecules as well as by Class I, but that the generation of T cells specific for this peptide are not effectively generated by DC loaded with PSA. No responses were found when the T cells that had been cultured with immune complex were stimulated with mature DC that had been pulsed with an HLA-A*0201 restricted HIV-1 gag peptide (data not shown).

Example X

T Cell Responses to DC Armed With PSA or PSA-m

DC express receptors that bind mannose and related carbohydrates. Accordingly, experiments were conducted to compare the T cell responses to DC that had been armed with PSA or PSA that had been conjugated to mannose. To do this, PSA was purchased from Scripps Laboratories (San Diego, Calif.). PSA was mannosylated as follows: 100 µg of PSA was combined with 100 µg α-D-mannopyranosylphenylisothiocyanate (a-D-M) and 2 µl N-methylmorpholine in 460 µl of PBS and stirred overnight at room temperature. Excess α-D-M was hydrolyzed by the addition of 100 µl of 1M Trizma-base (pH 9.5). Unconjugated mannose residues were removed by dialysis against PBS and stored at 4° C.

The T cells were exposed through two weekly rounds of stimulation to DC armed with PSA or PSA-m and CD4+ and CD8+ IFNγ responses measured after re-exposure to armed DC. To do this, as described in Example III, T cells were exposed to DC armed with PSA or mannosylated-PSA (PSA-M) and cultured. At day 14, T cells were restimulated with unarmed or antigen armed DC and numbers of CD4+ and CD8+ T cells producing IFNγ determined by flow cytometry. The results are shown in Table IV.

TABLE IV

Comparison of T Cell Responses to Dendritic Cells Armed With PSA or Mannosylated PSA

| | | IFNγ+ cells/10$^6$ | |
|---|---|---|---|
| Primary stimulation | Restimulation | CD4+ | CD8+ |
| O | PSA | 33 | 42 |
| PSA | O | 109 | 41 |
| PSA | PSA | 438 | 88 |
| PSA | PSA-M | 566 | 92 |
| O | PSA-M | 80 | 61 |
| PSA-M | O | 111 | 82 |
| PSA-M | PSA-M | 894 | 122 |
| PSA-M | PSA | 504 | 113 |

As show in Table IV, in three separate experiments, CD4+ T cell responses predominated within the activated cell population and were consistently higher when DC were loaded with PSA-m compared to responses to PSA armed DC. Small to modest increases (over controls) in number of activated CD8+ T cells were observed. However, the CD8+ T cell response to PSA-m was far below responses seen with Alt-6-PSA immune complexes (see FIG. 6).

Example XI

Clinical Studies

Patients suffering from recurring ovarian cancer were injected with 2 mg monoclonal antibody Alt2 per day, with a total of 1 to 10 such treatments and followed for disease progression and survival. Alt2 is a murine monoclonal IgG1 antibody to CA125. The antibody has a high affinity ($1\times10^{10}$ $M^{-1}$) and was modified, such as by photoactivation (partial reduction of disulfide bonds, see U.S. Pat. No. 6,086,873). All patients were tested for HAMA and CA125 before and after each injection by ELISA (HAMA, commercially available from Medac, Germany; CA125, commercially available from Centocor, USA). Seventy-five patients were tested for anti-idiotype antibodies (Ab$_2$) to Alt2 by ELISA (commercially available from AltaRex Corp., USA) and anti-CA125 antibodies by ELISA (AltaRex; see also Schultes et al., Cancer Immunol. Immunother. 46: 201 (1998)). For 17 patients, peripheral blood mononuclear cells (PBMC) were available before and after injection.

Figure 10A:
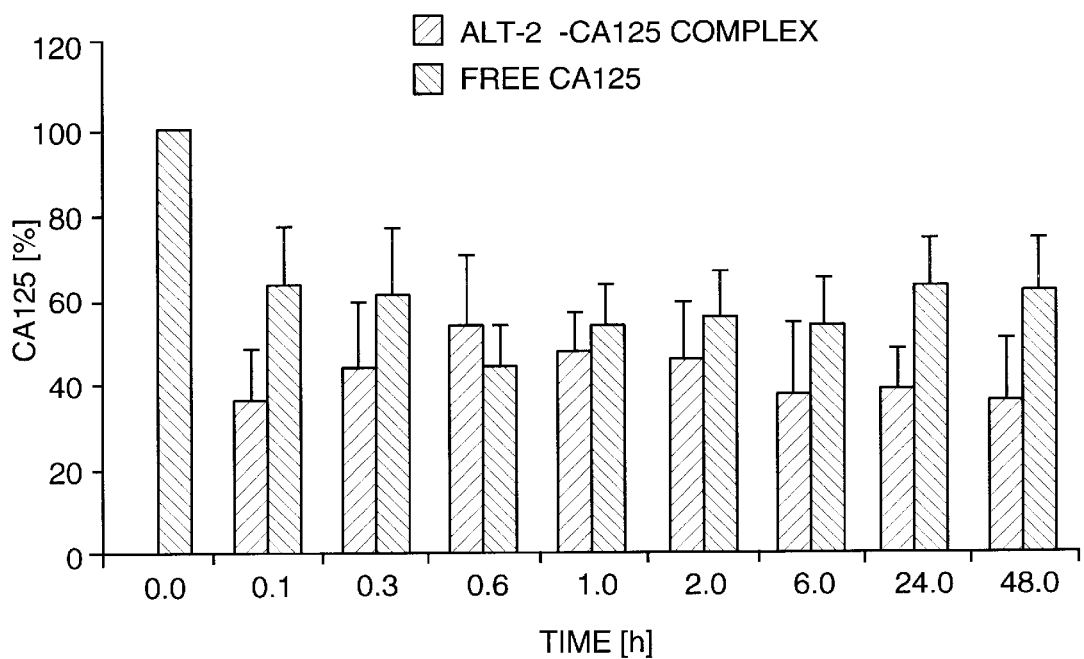
FIGS. 10A and 10B show the rate of complexation of anti-CA125 antibody, Alt-2, to circulating CA125 following injection of Alt-2. Specifically.
Figure 10B:
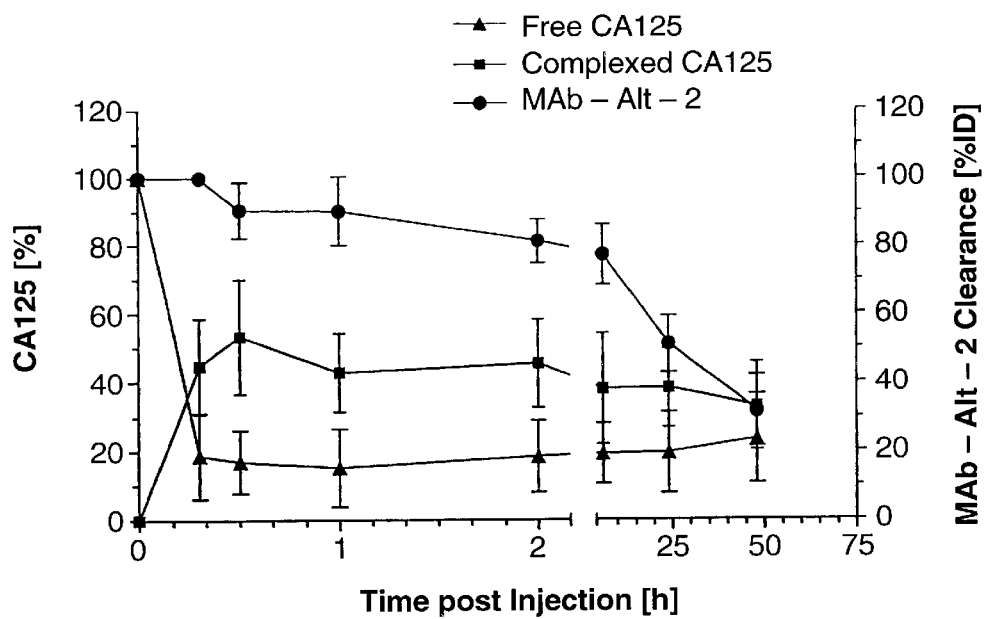

To determine how quickly the injected Alt2 antibody could form immune complexes with free CA125, CA125 was captured from serum samples (that were obtained at various time points after MAb Alt-2 injection) with the anti-CA125 antibody MAb-B27.1, which recognizes an epitope distinct from MAb Alt-2. After washing, tubes were incubated with $^{125}$I-MAb-Alt-2 or $^{125}$I-MAb OC125. This procedure allows for detection of CA125 bound MAb Alt-2 in the serum, indicated by decreased tracer binding of $^{125}$I-MAb Alt-2 in comparison to preinjection samples as well as decreased binding in comparison to $^{125}$I-MAb OC125. As shown in FIGS. 10A and 10B, MAb-Alt-2 was found to form complexes with CA125 within 30 minutes of injection of the antibody. These complexes cleared very slowly from circulation at the first MAb Alt-2 injection (see right half of FIG. 10B). The results show that MAb Alt-2 can bind to CA125 in circulation and form long circulating immune complexes. Consequently there is an opportunity of such complexes to be taken up by the immune system and undergo processing and presentation to T cells.

In addition, PBMC of the antibody-injected patients were analyzed for T cell proliferation to CA125 in a standard $^3$H-thymidine uptake assay without in vitro sensitization (for assay methods see, e.g., *Current Protocols in Immunology*, ed. John E. Coligan, John Wiley & Sons, Inc. 1993; *Current Protocols in Molecular Biology*, eds. Ausubel et al., John Wiley & Sons, Inc. 2000). The results are shown in FIGS. 11A–13B.

Figure 11A:
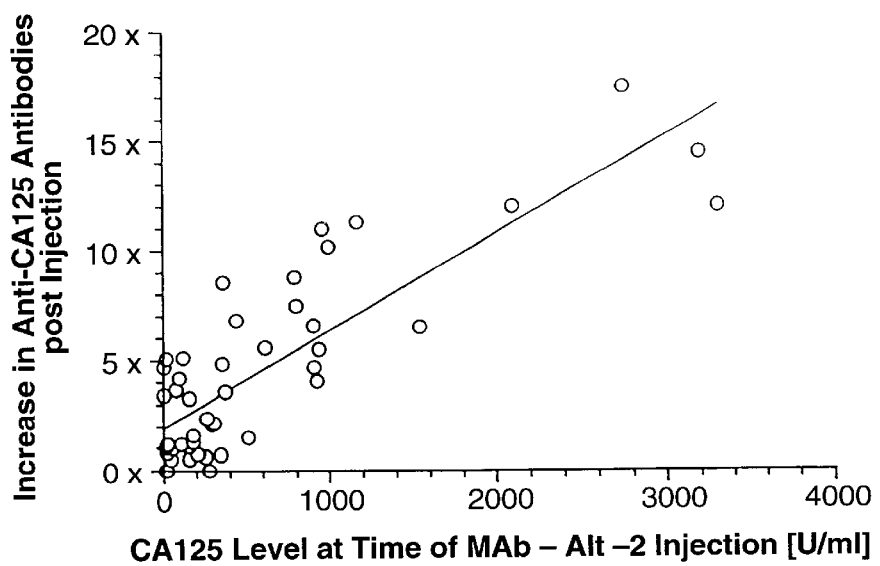
FIGS. 11A, 11B, and 11C are graphs showing the relationship between CA125 antigen specific B cell (FIG. 11A) and T cell (FIGS. 11B and 11C) responses, CA125 level, and patient survival. Specifically.
Figure 11B:
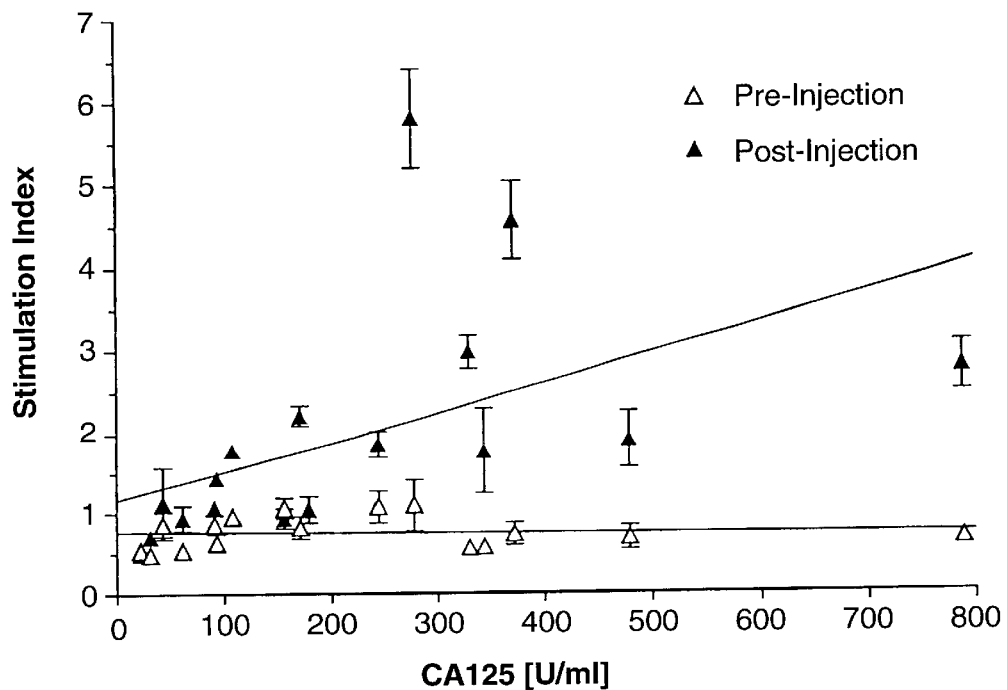
Figure 11C:
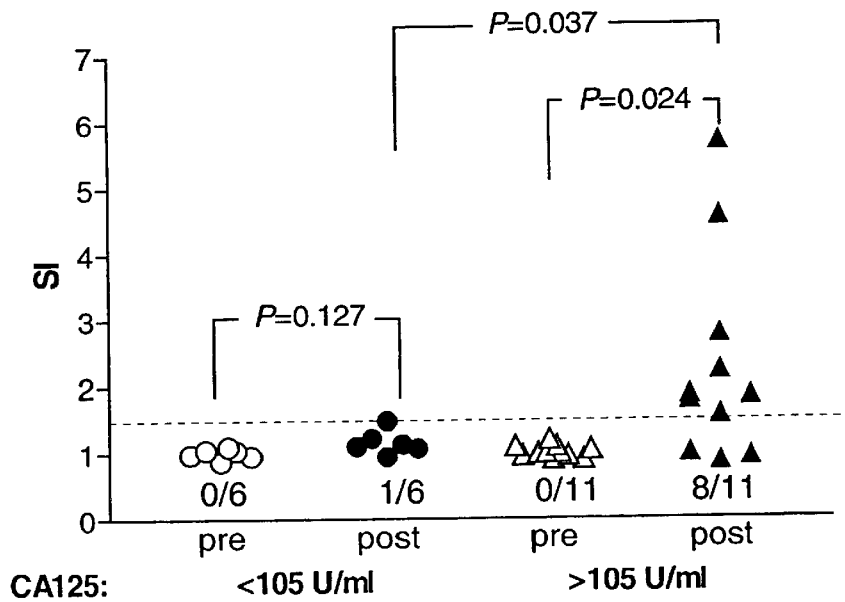
Figure 12:
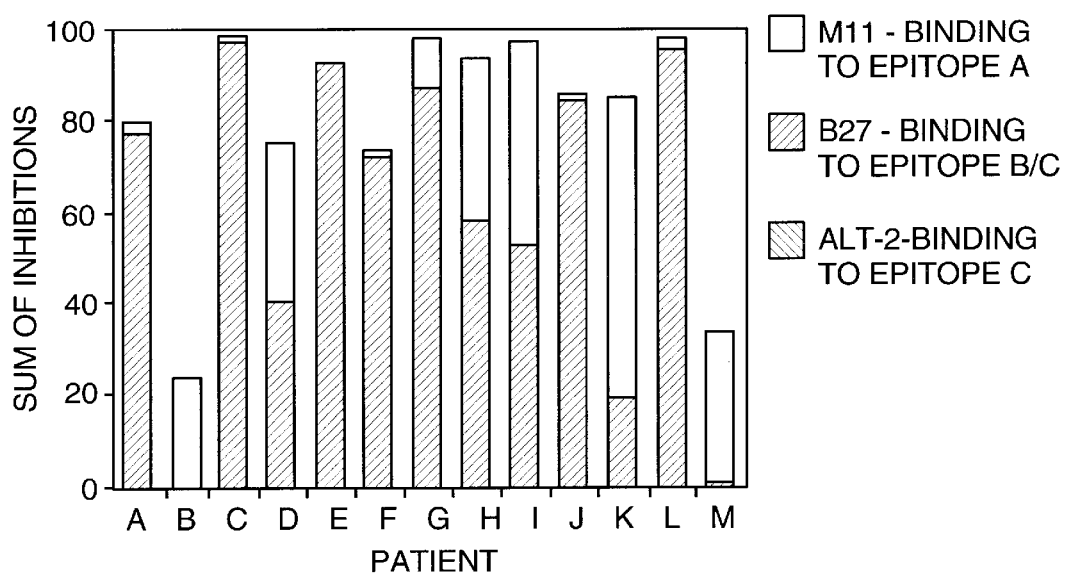
FIG. 12 is a bar graph showing the multi-epitopic nature of the response from anti-CA125 antibodies produced by thirteen patients.

Induction of humoral (Pearson r=0.8335, p<0.001) and cellular (p=0.037) anti-CA125 responses showed a correlation with the amount of circulating CA125 antigen present at the time of Alt2 injection (FIGS. 11A–11C). Neither B nor T cell responses specific for CA125 were detected in the pre-injection samples. Analysis of the patients' anti-CA125 antibodies revealed that they were directed against multiple epitopes of CA125 (FIG. 12). This analysis was done by inhibiting human α-CA125 antibody by various α-CA125 monoclonal antibodies that specifically bound to distinct epitopes on CA125.

Figure 13A:
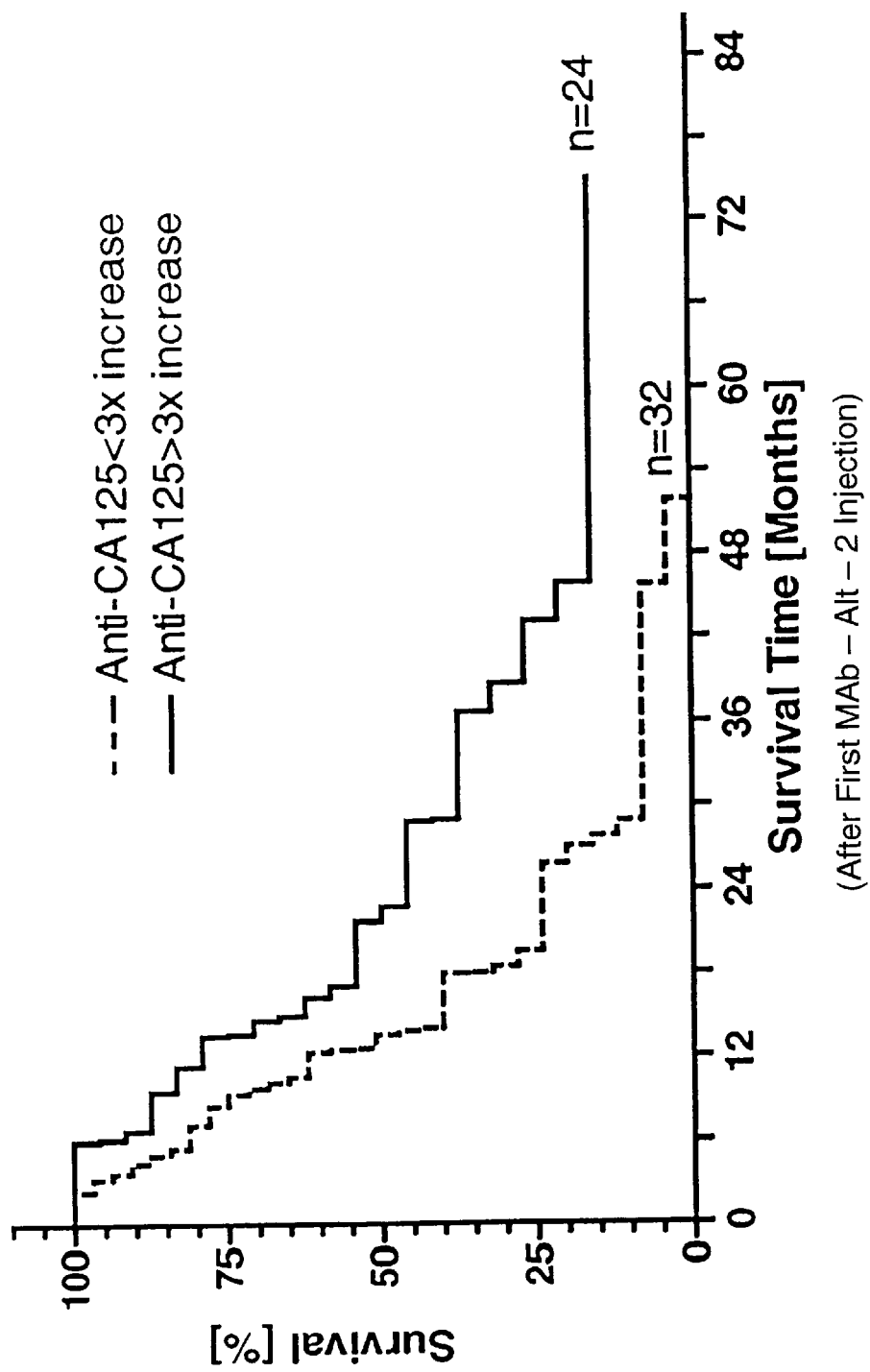
FIGS. 13A and 13B are survival curves of patients receiving injection of Alt-2. Specifically.
Figure 13B:
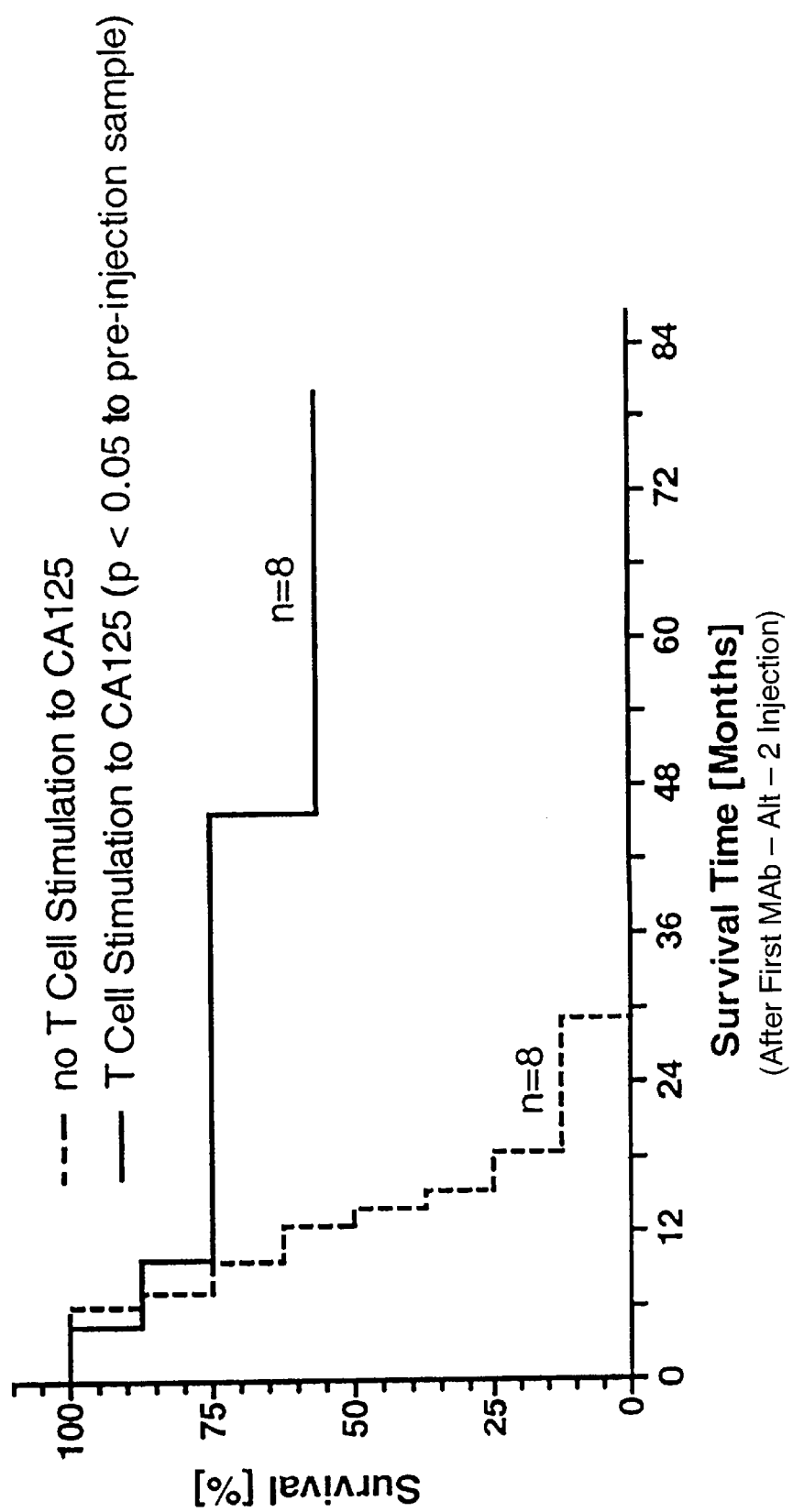

In addition, survival from the time of first antibody injection correlated with the generation of anti-CA125 antibodies (median survival 22.9 v. 13.5 months, p=0.0089; FIG. 13A) and generation of CA125-specific T cells (84 v. 13.2 months, p=0.0202; FIG. 13B) after Alt2 injection for anti-CA125 responders v. non-responders. These results demonstrate the following. The levels of circulating CA125 at time of Alt2 injection showed influence on the frequency and amount of immune responses induced to CA125 after injection of the antibody. Patients' anti-CA125 antibodies were found to be multi-epitopic (See FIG. 12). As FIGS. 13A and 13B show, survival after the first injection of Alt2 (plotted in Kaplan-Meier curves) was significantly longer in patients with CA125-specific antibodies (increase in titer>3 times pre-injection value), and in patients with CA125-specific T cells (SI>1.5) (log-rank test, p<0.01 and p<0.05 respectively).

Example XII

Effect of Complex Formation on Antigen Presentation

CA125 was purified from tissue culture supernatants of NIH:OVCAR-3 cells (commercially available from AltaRex Corp.) and PSA was purified from human seminal plasma (commercially available from Scripps, La Jolla, Calif.) using standard procedures. Photoactivated Alt2 antibody was as described previously (see Example VII). The anti-PSA antibody, Alt6 (commercially available from AltaRex Corp.), is a mouse IgG1 that binds to the region of amino acids 135 to 150 of PSA. HAMA was as described previously (see Example VI). Human dendritic cells were prepared from buffy coats by Ficoll-Hypaque and negative selection with anti-CD3, CD16 and CD19, followed by anti-mouse-IgG magnetics beads (Dynal). Cells were cultured in 1000 U/ml GM-CSF and 1000 U/ml IL-4 for 4 days.

Murine macrophages were isolated from the peritoneal cavity of Balb/c mice. Specific B cells were isolated from immunized mice by panning on antibody-coated petri dishes. Dendritic cells were loaded with antigen, antibody, or antigen-antibody complex at day 4 and matured with 10 ng/ml TNF-α and 50 U/ml IFN-α 4 hours later. Two stimulation rounds were performed before analyzing the cells for intracellular IFN-γ staining for either CD4 and CD8 T cells or for the release of IFN-γ into the culture supernatant.

Figure 14A:
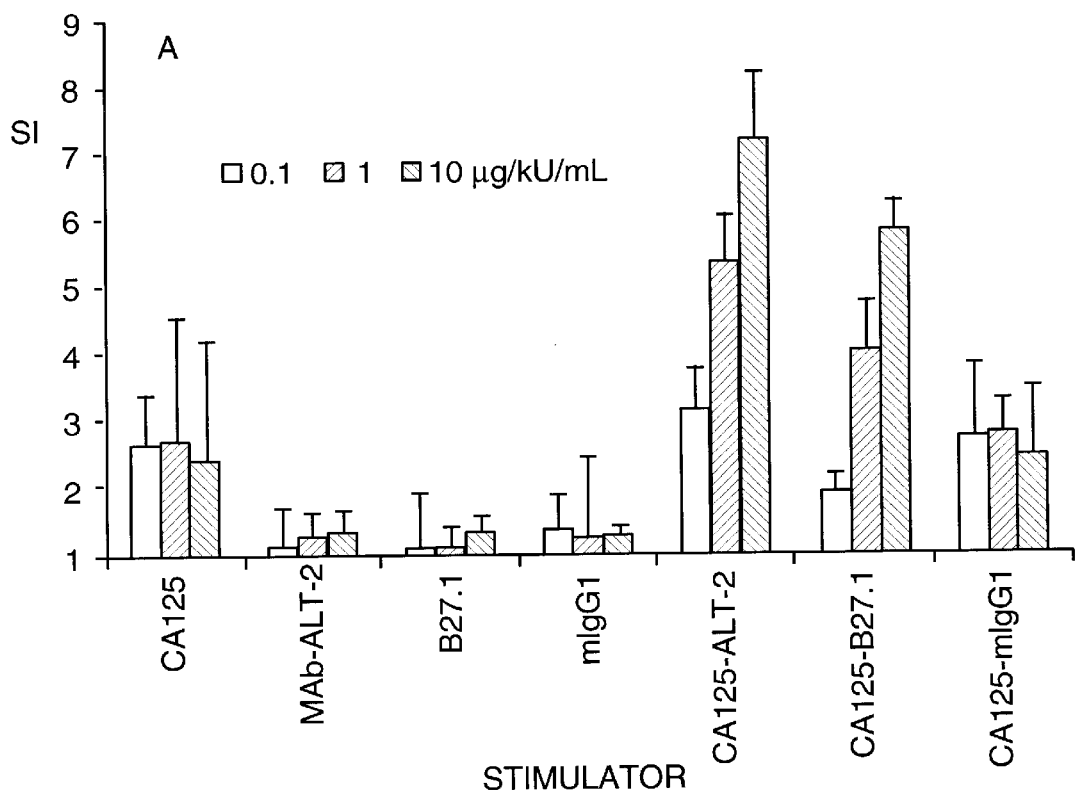
FIGS. 14A–14B show the preferential presentation of antigen complexed with antibody by antigen presenting cells such as macrophages and B cells. Specifically.
Figure 14B:
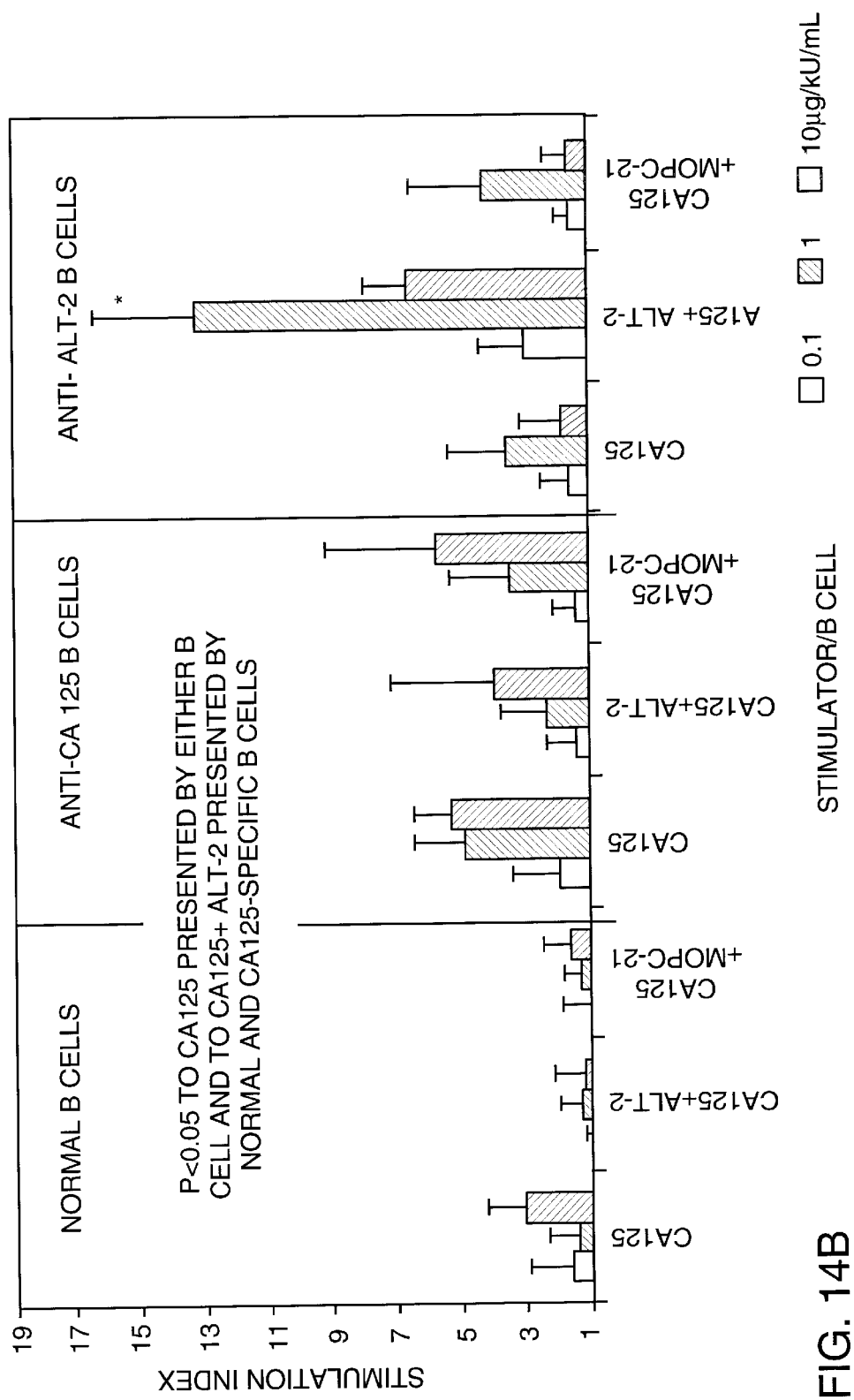

The results are shown in FIGS. 14A–14B. These results show that antigen complexed with specific antibody can be preferentially presented by professional APC such as macrophages (FIG. 14A) and B cells (FIG. 14B). Results from the antigen-antibody system with PSA and CA125 in dendritic cells support an enhanced presentation of the extracellular antigen on MHC class I when offered as an immune complex (see FIGS. 6, 8A, and 8B). Also, these results further confirmed the results shown in Table IV (above); namely that while mouse IgG1 alone binds weakly to dendritic cells (FIG. 2), the binding is enhanced by binding of specific antigen, and substantially enhanced in the presence of HAMA (FIGS. 3A–5B). Finally, these results demonstrate that dendritic cells present immune complexes better than non-complexed antigen (FIGS. 6, 8A, and 8B) and, upon repeated stimulation, the immune complexes shifted the immune response from a helper (CD4+) to a cytolytic (CD8+) T cell response (FIGS. 6 and 8B), indicating presentation of antigen-derived peptides on both MHC class I and class II.

Example XIII

Ex Vivo Therapeutic Treatment

A human-PBL-SCID/BG mouse model is used generally as described in Schultes et al., Hybridoma 18: 47–55 (1999). Human ovarian cancer cells NIH:OVCAR-NU-3 are passaged through nude mice and maintained at 37° C. and 5% $CO_2$ using RPMI 1640 medium supplemented with 2 mM L-glutamine and 10% fetal bovine serum Life-Technologies, Gaithersburg, Md.) SCID/BG mice are obtained from Taconic (Germantown, N.Y.). Tumors are developed in the SCID/BG mice by subcutaneous injection of 4×10$^6$ NIH:OVCAR-NU-3 tumor cells and three weeks incubation. Dendritic cells are loaded with CA125 antigen or with CA125 antigen and Alt2 antibody as described in Example III, with or without HAMA. The combination is then administered to the mouse either intraperitoneally or intravenously. This treatment is repeated every 2 to 3 weeks. Tumor burden and days of survival are monitored. It is expected that the dendritic cells loaded with the antigen-antibody complex have a greater anti-tumor effect than the dendritic cells loaded with antigen alone, and that the greatest effect is observed when the dendritic cells loaded with the antigen-antibody-HAMA complex are administered.

Example XIV

In Vivo Efficacy of an Antigen-Specific Monoclonal Antibody in Murine Animal Model The efficacy of the Alt1, Alt2 and Alt6 monoclonal antibodies (MAb) in viva and the role of antibody-antigen complexes in the induction of an immune response and anti-tumor responses were studied in murine animal models. The immunization of mice with Alt1, Alt2 and Alt6 MAb was studied to determine whether Alt1, Alt2 and Alt6 can (a) induce a specific immunity against the specific antigen, MUC1, CA125 or PSA, respectively, (b) protect the mice against subsequent tumor challenge; and (c) eradicate established tumors and/or increase survival.

These experiments were performed using DBA and Balb/c and human PBL-SCID/bg mice which allowed one to choose the best animal model for future experiments. Five groups of mice were immunized respectively with MAb, control MAb, and MAb/antigen complexes. Antigen and PBS controls were studied. The immunization and tumor induction procedures were identical to the ones used for previous studies. Survival curves were plotted using the Meir Kaplan Algorithm. Comparison of responses between various groups were analyzed using standard statistical procedures.

Specifically, to do these studies, the treatment groups described in Table V were set up using SCID/bg mice:

TABLE V

| Group | Mice Number | Treatment |
|---|---|---|
| 1 | 9 | phosphate buffered saline (PBS) i.v. |
| 2 | 9 | MOPC-21 i.v. |
| 3 | 9 | Alt-6 i.v. |
| 4 | 9 | Alt-6 plus PSA i.v. |
| 5 | 8 | PSA i.v. |
| 6 | 8 | Alt-6 s.c |
| 7 | 8 | MOPC-21 s.c. | i.v. (intravenous) injection: 50 µg of antibody and/or 10 µg of PSA
i.p. (intraperitoneal) injection: 100 µg of antibody and/or 20 µg PSA
s.c. (subcutaneous) injection: 50 µg of antibody Groups 1–5 received the first two injections intraperitoneally, and the next four intravenously Groups 6–7 received the first two injection intraperitoneally, and the next four subcutaneously with the adjuvant Quil A.

The treatment schedule was as follows in Table VI:

TABLE VI

| Day | procedure | comments |
|---|---|---|
| 1 | PBL (1 × 10⁷ human PBL/mouse) i.v. plus immunization, i.p. | PBL (peripheral blood leukocytes) from one HLA-A2+ donor |
| 8 | immunization, i.p. Dose 2 | |
| 12 | Bleeding for hIgG testing | 3 × 10⁶/mouse with 75% Matrigel |
| 18 | LnCap (tumor) inoculation s.c. | |
| 21 | immunization i.v./s.c. Dose 3 | |
| 29 | immunization i.v./s.c. Dose 4 | |
| 35 | immunization i.v./s.c. Dose 5 | |
| 42 | immunization i.v./s.c. Dose 6 | |
| 48 | Terminate mice/weigh tumor | When biggest tumor reached 10 × 19 mm |

Figure 15:
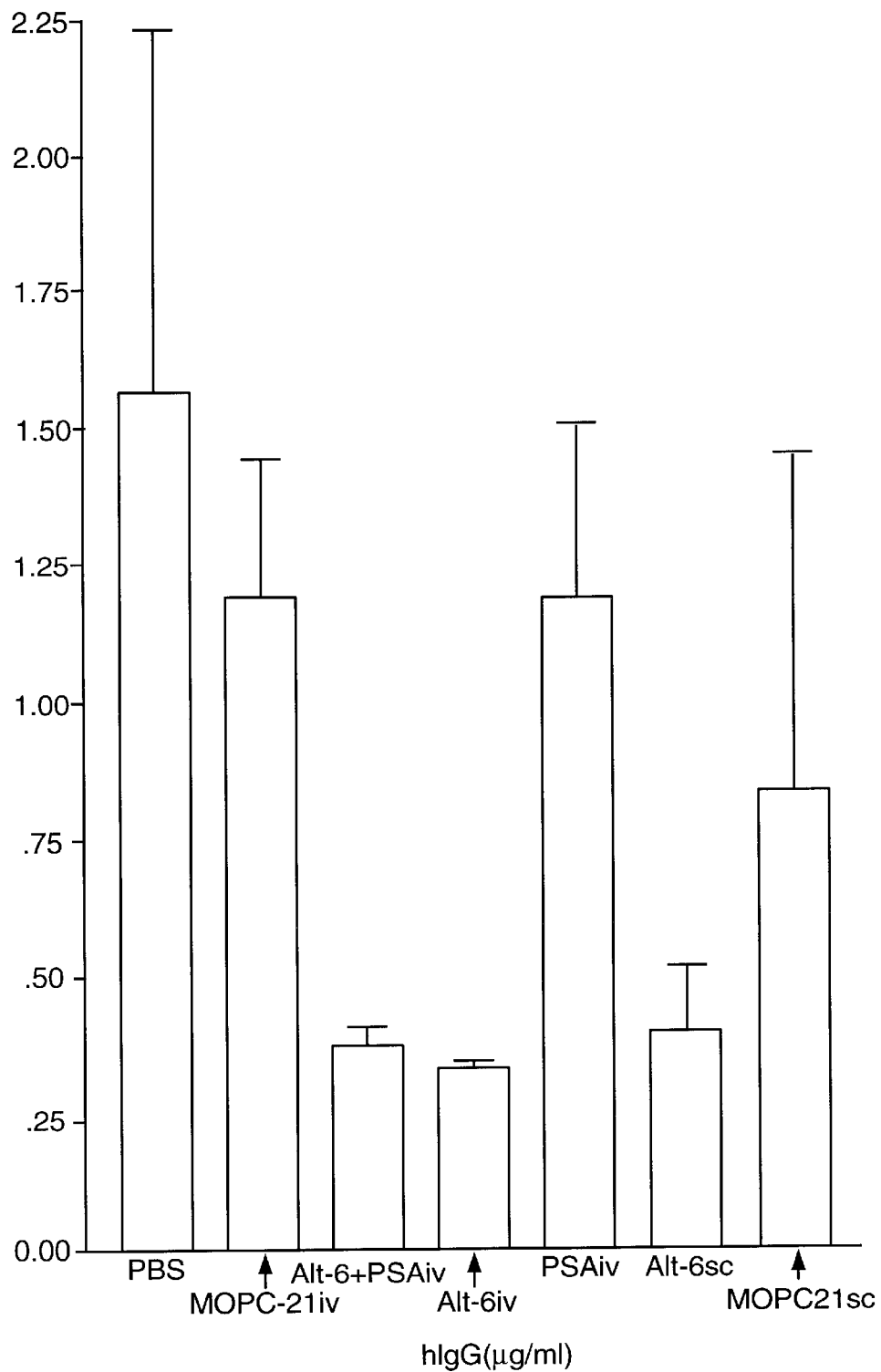
FIG. 15 is a bar graph showing the different levels of human IgG in reconstituted SCID/bg mice.

On Day 22, human IgG levels were measured (as mg/ml). As can be seen on FIG. 15, those mice injected with PBS only (i.e., Group 1) had the highest level of human IgG antibodies.

To measure successful reconstitution of human PBLs in the mice, serum human IgG was measured. These results are shown on Table VII.

TABLE VII

| Group | Number of mice | Number of mice with greater than 0.1 mg/ml hIgG | Percentage of mice with greater than 0.1 mg/ml hIgG |
|---|---|---|---|
| PBS i.v. | 9 | 5 | 56 |
| MOPC-21 i.v. | 9 | 7 | 78 |
| Alt-6 i.v. | 9 | 0 | 0 |
| Alt-6 + PSA i.v. | 9 | 2 | 22 |
| PSA i.v. | 8 | 6 | 75 |
| Alt-6 s.c | 8 | 4 | 50 |
| MOPC-21 s.c. | 8 | 3 | 38 |

All off the mice in all groups grew tumor (i.e., from the LnCap inoculation). These tumors were palpable 17 days after inoculation (i.e., Day 35). The tumors were measured twice a week.

Figure 16:
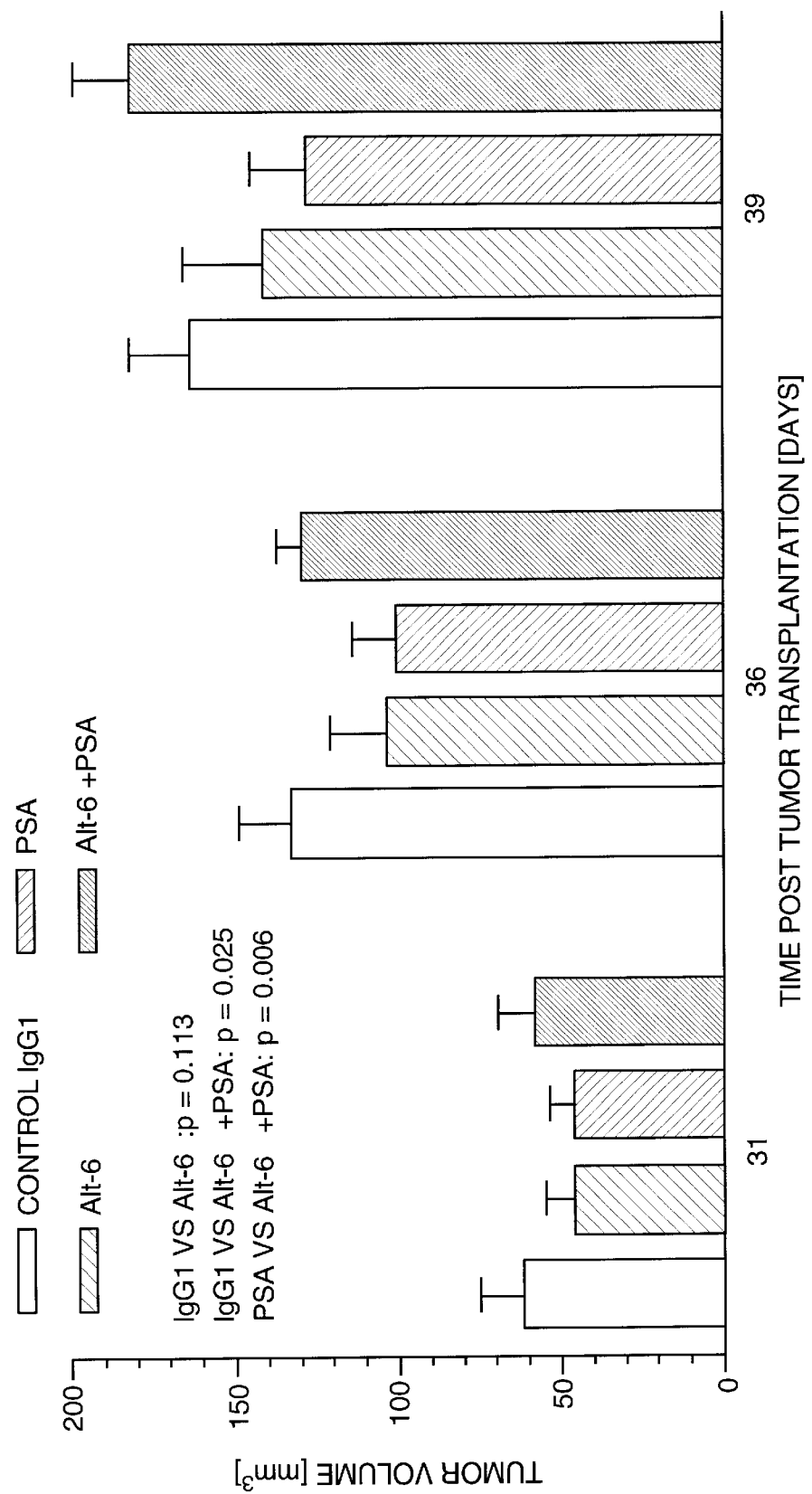
FIG. 16 is a bar graph showing the different tumor volumes in mice treated with control IgG1, Alt-6 only, PSA only, and the PSA/α-PSA immune complex.

As shown in FIG. 16, the mouse group injected with Alt-6 plus PSA i.v. demonstrated the best tumor suppression (Alt-6 plus PSA i.v. versus PSA iv; P=0.0477). The Alt-6 i.v. group also showed tumor suppression (as measured by tumor volume).

These results demonstrated that best anti-tumor effects were achieved in mice treated with the antibody-antigen complexes.

The humoral immune response was monitored by measuring the serum levels of Ab2 and Ab3 in ELISAs.

The cellular immune response was monitored according to routine laboratory procedures by measuring lymphocyte proliferation.

Example XV

Histopathological and Toxicological Studies

The tissue antigen specificity of Alt1 and Alt2 was examined by histopathological reactivity with both normal and tumor human tissues. The degree of heterogeneity in reactivity was recorded. This study was conducted by a commercial organization (Impath Inc.) under GLP conditions.

Acute and subacute toxicity of naked Alt1 and Alt2 was conducted in two species (rat and rabbits) by the division of the animal services at the University of Alberta. There was toxicity observed in acute or subacute studies.

Example XVI

Phase I Clinical Trial

Because there was data available on the "safety" of murine antibodies administered to humans, it was not expected that side effects were a dose limiting problem. However, standard criteria such as major organ toxicity and patient symptoms were followed utilizing GCP. As antibody doses did not have to be pushed to toxicity (the maximally tolerated dose) the major outcome became defining the most effective dose of antibody that elicited the desired defined immune response.

The patient population to be studied needed to be immune competent and have the target disease. A group of patients with MUC1 expressing tumor were enrolled in a three-dose Phase I trial with Alt-1 Based on studies with other immune therapies it was expected that the effective dose was in the 1–4 mg dose. Doses of 1, 2, and 4 mg were studied in the stated patient population. Toxicity criteria were monitored along with the immune response (primary endpoint). Evidence of therapeutic activity was detected by monitoring patient MUC1 levels (secondary endpoint). Six patients per dose level were treated. The 2 mg dose was most effective in inducing HAMA, Ab2, anti-MUC1 antibodies and MUC1-specific T cells, and showed the highest incidence of MUC1 serum level stabilization or decrease.

Equivalents

Those skilled in the art will recognize, or be able to ascertain, using no more than routine experimentation, numerous equivalents to the specific embodiments described specifically herein. Such equivalents are intended to be encompassed in the scope of the following claims.

We claim:

1. An immunotherapy method for a patient suffering from a disease associated with expression of prostate specific antigen (PSA), comprising administering to the patient a composition comprising said PSA antigen, an antibody immunoreactive with said PSA antigen, and a dendritic cells autologous to the patient, in an amount sufficient to induce a cytotoxic T lymphocyte (CTL) immune response to cells expressing PSA.

2. The method of claim 1, wherein the PSA antigen is complexed to the antibody.

3. The method of claim 1, wherein the dendritic cells are immature dendritic cells.

4. The method of claim 3, wherein the dendritic cells of the composition are complexed with said PSA antigen and said antibody, and stimulate a PSA-specific T cell response.

5. The method of claim 1, wherein the dendritic cells are dendritic cell precursors.

6. The method of claim 5, wherein the dendritic cells of the composition are complexed with said PSA and said antibody, and induce said CTL immune response.

7. The method of claim 1, wherein the patient is a human.

8. The method of claim 1, wherein administration of said composition activates a CD8+IFN-γ producing T cell response in the patient.

9. The method of claim 1, wherein administration of said composition activates a CD4±IFN-γ producing T cell response in the patient.

10. The method of claim 1, wherein administration of said composition activates a humoral immune response in the patient.

11. The method of claim 1, wherein the antibody includes an Fc portion that binds to an Fcγ receptor selected from the group consisting of an Fcγ Type I (CD64) receptor, an Fcγ Type II (CD32) receptor, and an Fcγ Type III (CD 16) receptor.

12. The method of claim 1 wherein the antibody is a xenotypic antibody to the patient.

13. The method of claim 12, wherein the xenotypic antibody elicits a host antixenotypic antibody response in the patient.

14. The method of claim 12, wherein host anti-xenotypic antibodies, immunoreactive with said xenotypic antibody, are present in the patient's blood prior to administering the composition.

15. The method of claim 12, wherein the xenotypic antibody is a murine monoclonal antibody.

16. The method of claim 15, wherein the murine monoclonal antibody is produced by the hybridoma having ATCC Number HB-12526.

17. The method of claim 12, wherein the composition further comprises human antixenotypic antibodies.

18. The method of claim 1, wherein the antibody is a single chain antibody.

19. The method of claim 1, wherein the method reduces the growth of prostate cancer cells in the patient.

20. The method of claim 1, wherein the method reduces the volume of a prostate tumor in the patient.

21. The method of claim 1, wherein said PSA antigen present in the composition is a peptide selected from the group consisting of FLTPKKLQCV (SEQ ID NO:2) and KLQCVDLHV (SEQ ID NO:3).

\* \* \* \* \*

UNITED STATES PATENT AND TRADEMARK OFFICE
CERTIFICATE OF CORRECTION

| | | |
|---|---|---|
| PATENT NO. | : 6,689,355 B2 | Page 1 of 1 |
| APPLICATION NO. | : 09/853268 | |
| DATED | : February 10, 2004 | |
| INVENTOR(S) | : Birgit C. Schultes | |

It is certified that error appears in the above-identified patent and that said Letters Patent is hereby corrected as shown below:

Claim 1, line 55, "a dendritic cells" should be --dendritic cells--.

Signed and Sealed this

Seventeenth Day of July, 2007

JON W. DUDAS
*Director of the United States Patent and Trademark Office*